(12) United States Patent
Brown et al.

(10) Patent No.: US 8,030,339 B2
(45) Date of Patent: Oct. 4, 2011

(54) IMIDAZOLE DERIVATIVES FOR THE TREATMENT OF ANXIETY AND RELATED DISEASES

(75) Inventors: William Dalby Brown, Saborg (DK); Janus S. Larsen, Holbæk (DK); Lene Teuber, Værløse (DK); David Tristram Brown, Albertslund (DK); Philip K. Ahring, Bagsværd (DK); Naheed Mirza, Birkerød (DK); Elsebet Østergaard Nielsen, København (DK)

(73) Assignee: Neurosearch A/S, Ballerup (DK)

( * ) Notice: Subject to any disclaimer, the term of this patent is extended or adjusted under 35 U.S.C. 154(b) by 494 days.

(21) Appl. No.: 12/083,375

(22) PCT Filed: Oct. 12, 2006

(86) PCT No.: PCT/EP2006/067315
§ 371 (c)(1),
(2), (4) Date: Aug. 7, 2008

(87) PCT Pub. No.: WO2007/042546
PCT Pub. Date: Apr. 19, 2007

(65) Prior Publication Data
US 2009/0233929 A1    Sep. 17, 2009

Related U.S. Application Data

(60) Provisional application No. 60/726,677, filed on Oct. 17, 2005.

(30) Foreign Application Priority Data

Oct. 14, 2005    (DK) .................................. 2005 01445

(51) Int. Cl.
| | |
|---|---|
| C07D 417/06 | (2006.01) |
| C07D 417/14 | (2006.01) |
| C07D 409/06 | (2006.01) |
| C07D 409/14 | (2006.01) |
| C07D 405/06 | (2006.01) |
| C07D 405/14 | (2006.01) |
| C07D 401/06 | (2006.01) |
| C07D 401/14 | (2006.01) |
| C07D 403/06 | (2006.01) |
| C07D 403/14 | (2006.01) |
| C07D 233/64 | (2006.01) |
| A61K 31/506 | (2006.01) |
| A61K 31/444 | (2006.01) |
| A61K 31/4439 | (2006.01) |
| A61K 31/427 | (2006.01) |
| A61K 31/4178 | (2006.01) |
| A61K 31/4164 | (2006.01) |

(52) U.S. Cl. ........ 514/400; 514/397; 514/341; 514/256; 514/365; 514/333; 514/342; 548/333.5; 548/314.4; 548/200; 548/315.4; 548/312.4; 546/274.7; 546/256; 546/269.7; 544/333; 544/310

(58) Field of Classification Search .................. 514/400, 514/397, 341, 256, 365, 333, 342; 544/333, 544/310; 546/274.7, 256, 269.7; 548/333.5, 548/314.4, 200, 315.4, 312.4
See application file for complete search history.

(56) References Cited

U.S. PATENT DOCUMENTS 4,952,698 A * 8/1990 Biere et al. .................... 548/131

FOREIGN PATENT DOCUMENTS

| WO | WO-88/01268 A1 | 2/1988 |
| WO | WO-03/093263 A1 | 11/2003 |
| WO | WO-2004/041809 A2 | 5/2004 |

* cited by examiner

*Primary Examiner* — Joseph Kosack
*Assistant Examiner* — Matthew Coughlin
(74) *Attorney, Agent, or Firm* — Birch, Stewart, Kolasch & Birch, LLP

(57) ABSTRACT

This invention relates to novel imidazole derivatives, pharmaceutical compositions containing these compounds, and methods of treatment therewith.

The compounds of the invention are useful in the treatment of central nervous system diseases and disorders, which are responsive to modulation of the $GABA_A$ receptor complex, and in particular for combating anxiety and related diseases.

8 Claims, No Drawings

IMIDAZOLE DERIVATIVES FOR THE TREATMENT OF ANXIETY AND RELATED DISEASES

TECHNICAL FIELD

This invention relates to novel imidazole derivatives, pharmaceutical compositions containing these compounds, and methods of treatment therewith.

The compounds of the invention are useful in the treatment of central nervous system diseases and disorders, which are responsive to modulation of the $GABA_A$ receptor complex, and in particular for combating anxiety and related diseases.

BACKGROUND ART

The modulatory sites on the $GABA_A$ receptor complex, such as for example the benzodiazepine binding site, are the targets for anxiolytic drugs, such as the classical anxiolytic benzodiazepines. However, they are associated with a number of undesirable features.

Multiple isoforms of the $GABA_A$ receptor exist; each receptor is a pentameric complex comprising subunits drawn from $\alpha_{1-6}$, $\beta_{1-3}$, $\gamma_{1-3}$, $\delta$, $\epsilon$, and $\theta$ subunit isoforms. The classical anxiolytic benzodiazepines show no subtype selectivity. It has been suggested that one of the key elements in the disadvantages of the classical benzodiazepanes (such as sedation, dependency, and cognitive impairment) is relates to the $\alpha 1$ subunit of the $GABA_A$ receptors. Thus compounds with selectivity for the $\alpha 2$ and/or $\alpha 3$ subunits over the $\alpha 1$ subunit are expected to have an improved side effect profile.

Thus, there is still a strong need for compounds with an optimised pharmacological profile. Furthermore, there is a strong need to find effective compounds without unwanted side effects associated with older compounds.

SUMMARY OF THE INVENTION

In its first aspect, the invention provides a compound of Formula I:

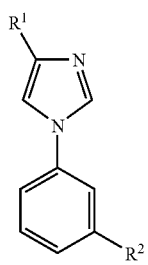

any of its isomers or any mixture of its isomers, or a pharmaceutically acceptable salt thereof,
wherein $R^1$ and $R^2$ are defined as below.

In its second aspect, the invention provides a pharmaceutical composition, comprising a therapeutically effective amount of a compound of the invention, any of its isomers or any mixture of its isomers, or a pharmaceutically acceptable salt thereof, together with at least one pharmaceutically acceptable carrier, excipient or diluent.

In a further aspect, the invention provides the use of a compound of the invention, any of its isomers or any mixture of its isomers, or a pharmaceutically acceptable salt thereof, for the manufacture of a pharmaceutical composition for the treatment, prevention or alleviation of a disease or a disorder or a condition of a mammal, including a human, which disease, disorder or condition is responsive to modulation of the $GABA_A$ receptor complex in the central nervous system.

In a still further aspect, the invention relates to a method for treatment, prevention or alleviation of a disease or a disorder or a condition of a living animal body, including a human, which disorder, disease or condition is responsive to modulation of the $GABA_A$ receptor complex in the central nervous system, which method comprises the step of administering to such a living animal body in need thereof a therapeutically effective amount of a compound of the invention, any of its isomers or any mixture of its isomers, or a pharmaceutically acceptable salt thereof.

Other objects of the invention will be apparent to the person skilled in the art from the following detailed description and examples.

DETAILED DISCLOSURE OF THE INVENTION

Imidazole Derivatives

In its first aspect the present invention provides a compound of the general formula (I):

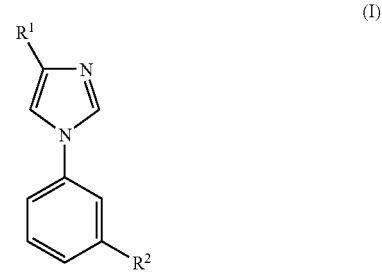

any of its isomers or any mixture of its isomers,
or a pharmaceutically acceptable salt thereof,
wherein
$R^1$ represents $-COR^3$;
  wherein $R^3$ represents hydrogen, alkyl, cycloalkyl, cycloalkylakyl, alkenyl, alkynyl, $-NR'R''$, $-(CH_2-O)_m$-aryl or $-(CH_2-O)_m$-heteroaryl;
    wherein m is 0 or 1; and
    which aryl or heteroaryl group is optionally substituted with one or more substituents independently selected from the group consisting of:
      halo, hydroxy, $R^a R^b N-$, $R^a R^b N$-alkyl, cyano, nitro, trifluoromethyl, trifluoromethoxy, alkoxy, cycloalkoxy, $R^a-(C=O)-$, $R^a-O-(C=O)-$, alkyl, cycloalkyl, cycloalkylalkyl, alkenyl, and alkynyl;
        wherein $R^a$ and $R^b$ independent of each other are hydrogen or alkyl; and
    R' and R'' independent of each other are hydrogen, alkyl, alkenyl, alkynyl, hydroxy, hydroxyalkyl, alkoxy, or alkoxyalkyl; or
    R' and R'' together with the nitrogen to which they are attached form a 5- to 7-membered heterocyclic ring, which heterocyclic ring may optionally comprise as a ring member, one oxygen atom, and/or one additional nitrogen atom, and/or one carbon-carbon double bond, and/or one carbon-nitrogen bond; and which heterocyclic ring may optionally be substituted with trifluoromethyl, alkyl, hydroxy, hydroxyalkyl, or —NR'''R'''';
wherein R''' and R'''' independently of each other are hydrogen or alkyl; and $R^2$ represents
halo, nitro, aryl or heteroaryl;
which aryl or heteroaryl group is optionally substituted with one or more substituents independently selected from the group consisting of:
halo, hydroxy, $R^dR^eN$—, $R^dR^eN$—(C=O)—, cyano, nitro, trifluoromethyl, trifluoromethoxy, alkoxy, cycloalkoxy, $R^d$—(C=O)—, $R^d$—O—(C=O)—, alkyl, cycloalkyl, cycloalkylalkyl, alkenyl, and alkynyl;
wherein $R^d$ and $R^e$ independent of each other are hydrogen or alkyl.

In one embodiment, $R^1$ represents —$COR^3$; wherein $R^3$ represents —NR'R''. In a special embodiment, R' represents hydrogen and R'' represents alkyl, such as methyl, propyl or isopropyl. In a further embodiment, R' represents alkyl, such as methyl, and R'' represents alkyl, such as methyl. In a still further embodiment, R' represents hydrogen and R'' represents alkenyl, such as allyl. In a further embodiment, R' represents hydrogen and R'' represents hydroxyalkyl, such as hydroxyethyl or 2-hydroxy-1-methyl.ethyl. In a still further embodiment, R' represents hydrogen and R'' represents alkoxyalkyl, such as methoxyethyl or 2-methoxy-1-methyl-ethyl. In a further embodiment, R' represents alkyl, such as methyl and R'' represents alkoxy, such as methoxy.

In a further embodiment, $R^1$ represents —$COR^3$; wherein $R^3$ represents —NR'R'', wherein R' and R'' together with the nitrogen to which they are attached form a 5- to 7-membered heterocyclic ring,
which heterocyclic ring may optionally comprise as a ring member, one oxygen atom, and/or one additional nitrogen atom, and/or one carbon-carbon double bond, and/or one carbon-nitrogen bond; and
which heterocyclic ring may optionally be substituted with trifluoromethyl, alkyl, hydroxy, hydroxyalkyl, or —NR'''R'''';
wherein R''' and R'''' independently of each other are hydrogen or alkyl.

In a special embodiment, $R^3$ represents optionally substituted morpholinyl, such as morpholin-4-yl. In a further embodiment, $R^3$ represents optionally substituted pyrrolidinyl, such as pyrrolidin-1-yl. In a still further embodiment, $R^3$ represents optionally substituted piperazinyl, such as 4-methyl-piperazin-1-yl.

In a further embodiment, $R^1$ represents —$COR^3$; wherein $R^3$ represents —$(CH_2$—$O)_m$-aryl; which aryl group is optionally substituted with one or more substituents independently selected from the group consisting of:
halo, hydroxy, $R^aR^bN$—, $R^aR^bN$-alkyl, cyano, nitro, trifluoromethyl, trifluoromethoxy, alkoxy, cycloalkoxy, $R^a$—(C=O)—, $R^a$—O—(C=O)—, alkyl, cycloalkyl, cycloalkylalkyl, alkenyl, and alkynyl;
wherein $R^a$ and $R^b$ independent of each other are hydrogen or alkyl.

In a special embodiment, $R^1$ represents —$COR^3$; wherein $R^3$ represents optionally substituted aryl, such as phenyl.

In a still further special embodiment, $R^3$ represents optionally substituted phenyl, such as halophenyl or alkoxyphenyl. In a further special, $R^3$ represents halophenyl, such as fluorophenyl, such as 3-fluorophenyl or 4-fluorophenyl. In a still further embodiment, $R^3$ represents optionally substituted alkoxyphenyl, such as methoxyphenyl, such as 2-methoxyphenyl, 3-methoxyphenyl or 4-methoxyphenyl.

In a still further embodiment, $R^1$ represents —$COR^3$; wherein $R^3$ represents —$(CH_2$—$O)_m$-heteroaryl; which heteroaryl group is optionally substituted with one or more substituents independently selected from the group consisting of:
halo, hydroxy, $R^aR^bN$—, $R^aR^bN$-alkyl, cyano, nitro, trifluoromethyl, trifluoromethoxy, alkoxy, cycloalkoxy, $R^a$—(C=O)—, $R^a$—O—(C=O)—, alkyl, cycloalkyl, cycloalkylalkyl, alkenyl, and alkynyl;
wherein $R^a$ and $R^b$ independent of each other are hydrogen or alkyl.

In a further embodiment, $R^1$ represents —$COR^3$; wherein $R^3$ represents —$(CH_2$—$O)$-(optionally substituted heteroaryl), such as pyridinyl-oxymethyl, such as pyridin-3-yl-oxymethyl.

In a still further special embodiment, $R^1$ represents —$COR^3$; wherein $R^3$ represents an optionally substituted heteroaryl.

In a special embodiment, $R^3$ represents optionally substituted pyridyl. In a further embodiment, $R^3$ represents pyridyl, such as pyridin-2-yl. In a still further embodiment, $R^3$ represents alkyl-pyridyl, such as methyl-pyridyl, such as 3-methyl-pyridin-2-yl or 4-methyl-pyridin-2-yl.

In a further embodiment, $R^3$ represents optionally substituted pyrimidyl. In a further embodiment, $R^3$ represents pyrimidyl, such as pyrimidin-2-yl.

In a still further embodiment, $R^3$ represents optionally substituted thiazolyl. In a special embodiment, $R^3$ represents thiazolyl, such as thiazol-2-yl. In a further embodiment, $R^3$ represents alkyl-thiazolyl, such as methyl-thiazolyl such as 5-methyl-thiazol-2-yl.

In a still further embodiment, $R^3$ represents optionally substituted imidazolyl. In a special embodiment, $R^3$ represents imidazolyl, such as imidazol-2-yl. In a further embodiment, $R^3$ represents alkyl-imidazolyl, such as methyl-imidazolyl, ethyl-imidazolyl or isopropyl-imidazolyl such as 1-methyl-imidazolyl-2-yl, 1-ethyl-imidazol-2-yl or 1-isopropyl-imidazol-2-yl. In a still further embodiment, $R^3$ represents hydroxyalkyl-imidazolyl, such as hydroxyethyl-imidazolyl, such as (2-hydroxyethyl)-imidazol-2-yl. In a further embodiment, $R^3$ represents alkoxyalkyl-imidazolyl, such as methoxyethyl-imidazolyl, such as (2-methoxyethyl)-imidazol-2-yl.

In a further embodiment, $R^3$ represents optionally substituted furyl. In a special embodiment, $R^3$ represents furyl, such as furan-2-yl.

In a still further embodiment, $R^3$ represents optionally substituted pyrazolyl, such as pyrazolyl, such as pyrazol-1-yl.

In a further embodiment, $R^3$ represents optionally substituted pyrrolyl, such as pyrrolyl, such as pyrrol-1-yl.

In a further embodiment, $R^1$ represents —$COR^3$; wherein $R^3$ represents alkyl, such as n-butyl.

In a further embodiment, $R^2$ represents halo or nitro. In a special embodiment, $R^2$ represents halo such as bromo. In a further embodiment, $R^2$ represents nitro.

In a still further embodiment, $R^2$ represents aryl, which aryl group is optionally substituted with one or more substituents independently selected from the group consisting of:
halo, hydroxy, $R^dR^eN$—, $R^dR^eN$-alkyl, $R^dR^eN$—(C=O)—, cyano, nitro, trifluoromethyl, trifluoromethoxy, alkoxy, cycloalkoxy, $R^d$—(C=O)—, $R^d$—O—(C=O)—, alkyl, cycloalkyl, cycloalkylalkyl, alkenyl, and alkynyl;
wherein $R^d$ and $R^e$ independent of each other are hydrogen or alkyl.

In a special embodiment, $R^2$ represents optionally substituted phenyl, such as phenyl. In a further embodiment, $R^2$ represents alkoxy-halo-phenyl, such as methoxy-fluoro-phenyl, such as 3-fluoro-2-methoxy-phenyl, 5-fluoro-2-methoxy-phenyl or 6-fluoro-2-methoxy-phenyl. In a still further embodiment, $R^2$ represents alkoxy-phenyl, such as methoxy-phenyl, such as 2-methoxy-phenyl. In a further embodiment, $R^2$ represents cyano-phenyl, such as 2-cyano-phenyl. In a still further embodiment, $R^2$ represents halo-phenyl, such as chloro-phenyl, such as 2-chloro-phenyl. In a further embodiment, $R^2$ represents trifluoromethoxy-phenyl, such as 2-trifluoromethoxy-phenyl.

In a still further embodiment, $R^2$ represents heteroaryl, which heteroaryl group is optionally substituted with one or more substituents independently selected from the group consisting of:

halo, hydroxy, $R^dR^eN-$, $R^dR^eN$-alkyl, $R^dR^eN-$(C=O)—, cyano, nitro, trifluoromethyl, trifluoromethoxy, alkoxy, cycloalkoxy, $R^d$—(C=O)—, $R^d$—O—(C=O)—, alkyl, cycloalkyl, cycloalkylalkyl, alkenyl, and alkynyl;
  wherein $R^d$ and $R^e$ independent of each other are hydrogen or alkyl.

In a special embodiment, $R^2$ represents optionally substituted pyridyl. In a further embodiment, $R^2$ represents halopyridyl, such as fluoropyridyl or chloropyridyl, such as 2-fluoropyridin-3-yl, 2-fluoropyridin-4-yl and 2-chloropyridin-3-yl. In a further embodiment, $R^2$ represents dihalopyridyl, such as difluoropyridyl, such as 2,4-difluoropyridin-3-yl. In a still further embodiment, $R^2$ represents dialkoxypyridyl, such as dimethoxypyridyl, such as 2,4-dimethoxypyridin-5-yl.

In a special embodiment the chemical compound of the invention is 1-(3-Nitro-phenyl)-1H-imidazole-4-carboxylic acid dimethylamide;
1-(3-Nitro-phenyl)-1H-imidazole-4-carboxylic acid methylamide;
1-(3-Nitro-phenyl)-1H-imidazole-4-carboxylic acid (2-hydroxy-ethyl)-amide;
Morpholin-4-yl-[1-(3-nitro-phenyl)-1H-imidazol-4-yl]-methanone;
1-(3-Nitro-phenyl)-1H-imidazole-4-carboxylic acid allylamide;
1-(3-Nitro-phenyl)-1H-imidazole-4-carboxylic acid propylamide;
1-(3-Nitro-phenyl)-1H-imidazole-4-carboxylic acid (2-methoxy-ethyl)-amide;
1-(3-Nitro-phenyl)-1H-imidazole-4-carboxylic acid (2-methoxy-1-methyl-ethyl)-amide;
1-(3-Nitro-phenyl)-1H-imidazole-4-carboxylic acid (2-hydroxy-1-methyl-ethyl)-amide;
1-(3-Nitro-phenyl)-1H-imidazole-4-carboxylic acid isopropylamide;
(4-Methyl-piperazin-1-yl)-[1-(3-nitro-phenyl)-1H-imidazol-4-yl]-methanone;
[1-(3-Nitro-phenyl)-1H-imidazol-4-yl]-pyrrolidin-1-yl-methanone;
1-[1-(3-Bromo-phenyl)-1H-imidazol-4-yl]-2-(pyridin-3-yloxy)-ethanone;
[1-(3-Bromo-phenyl)-1H-imidazol-4-yl]-phenyl-methanone;
(1-Biphenyl-3-yl-1H-imidazol-4-yl)-phenyl-methanone;
1-Biphenyl-3-yl-1H-imidazole-4-carboxylic acid methoxy-methyl-amide;
1-(5'-Fluoro-2'-methoxy-biphenyl-3-yl)-1H-imidazole-4-carboxylic acid methoxy-methyl-amide;
1-(2'-Methoxy-biphenyl-3-yl)-1H-imidazole-4-carboxylic acid methoxy-methyl-amide;
1-(2'-Cyano-biphenyl-3-yl)-1H-imidazole-4-carboxylic acid methoxy-methyl-amide;
1-(2'-Chloro-biphenyl-3-yl)-1H-imidazole-4-carboxylic acid methoxy-methyl-amide;
1-(2'-Trifluoromethoxy-biphenyl-3-yl)-1H-imidazole-4-carboxylic acid methoxy-methyl-amide;
1-(6'-Fluoro-2'-methoxy-biphenyl-3-yl)-1H-imidazole-4-carboxylic acid methoxy-methyl-amide;
1-(3'-Fluoro-2'-methoxy-biphenyl-3-yl)-1H-imidazole-4-carboxylic acid methoxy-methyl-amide;
1-[3-(2-Fluoro-pyridin-3-yl)-phenyl]-1H-imidazole-4-carboxylic acid methoxy-methyl-amide;
1-[3-(2,4-Difluoro-pyridin-3-yl)-phenyl]-1H-imidazole-4-carboxylic acid methoxy-methyl-amide;
1-[3-(2-Fluoro-pyridin-4-yl)-phenyl]-1H-imidazole-4-carboxylic acid methoxy-methyl-amide;
1-[3-(2-Chloro-pyridin-3-yl)-phenyl]-1H-imidazole-4-carboxylic acid methoxy-methyl-amide;
1-[3-(2,4-Dimethoxy-pyrimidin-5-yl)-phenyl]-1H-imidazole-4-carboxylic acid methoxy-methyl-amide;
(1-Biphenyl-3-yl-1H-imidazol-4-yl)-pyridin-2-yl-methanone;
[1-(5'-Fluoro-2'-methoxy-biphenyl-3-yl)-1H-imidazol-4-yl]-pyridin-2-yl-methanone;
[1-(5'-Fluoro-2'-methoxy-biphenyl-3-yl)-1H-imidazol-4-yl]-(3-methyl-pyridin-2-yl)-methanone;
[1-(5'-Fluoro-2'-methoxy-biphenyl-3-yl)-1H-imidazol-4-yl]-(4-methyl-pyridin-2-yl)-methanone;
[1-(5'-Fluoro-2'-methoxy-biphenyl-3-yl)-1H-imidazol-4-yl]-pyrimidin-2-yl-methanone;
(1-Biphenyl-3-yl-1H-imidazol-4-yl)-(4-fluoro-phenyl)-methanone;
(1-Biphenyl-3-yl-1H-imidazol-4-yl)-(3-fluoro-phenyl)-methanone;
(1-Biphenyl-3-yl-1H-imidazol-4-yl)-(4-methoxy-phenyl)-methanone;
(1-Biphenyl-3-yl-1H-imidazol-4-yl)-(3-methoxy-phenyl)-methanone;
1-(1-Biphenyl-3-yl-1H-imidazol-4-yl)-pentan-1-one;
(1-Biphenyl-3-yl-1H-imidazol-4-yl)-(2-methoxy-phenyl)-methanone;
(1-Biphenyl-3-yl-1H-imidazol-4-yl)-thiazol-2-yl-methanone;
(1-Biphenyl-3-yl-1H-imidazol-4-yl)-furan-2-yl-methanone;
[1-(5'-Fluoro-2'-methoxy-biphenyl-3-yl)-1H-imidazol-4-yl]-thiazol-2-yl-methanone;
[1-(5'-Fluoro-2'-methoxy-biphenyl-3-yl)-1H-imidazol-4-yl]-furan-2-yl-methanone;
[1-(5'-Fluoro-2'-methoxy-biphenyl-3-yl)-1H-imidazol-4-yl]-(5-methyl-thiazol-2-yl)-methanone;
[1-(5'-Fluoro-2'-methoxy-biphenyl-3-yl)-1H-imidazol-4-yl]-(1-methyl-imidazol-2-yl)-methanone;
(1-Ethoxymethyl-1H-imidazol-2-yl)-[1-(5'-fluoro-2'-methoxy-biphenyl-3-yl)-1H-imidazol-4-yl]-methanone;
(1-Ethyl-1H-imidazol-2-yl)-[1-(5'-fluoro-2'-methoxy-biphenyl-3-yl)-1H-imidazol-4-yl]-methanone;
(1-i-Propyl-1H-imidazol-2-yl)-[1-(5'-fluoro-2'-methoxy-biphenyl-3-yl)-1H-imidazol-4-yl]-methanone;
(1-(2-Hydroxyethyl)-1H-imidazol-2-yl)-[1-(5'-fluoro-2'-methoxy-biphenyl-3-yl)-1H-imidazol-4-yl]-methanone;
(1-(2-Methoxyethyl)-1H-imidazol-2-yl)-[1-(5'-fluoro-2'-methoxy-biphenyl-3-yl)-1H-imidazol-4-yl]-methanone;
[1-(2'-Methoxy-biphenyl-3-yl)-1H-imidazol-4-yl]-pyridin-2-yl-methanone;
[1-(2'-Methoxy-biphenyl-3-yl)-1H-imidazol-4-yl]-(3-methyl-pyridin-2-yl)-methanone;
[1-(2'-Methoxy-biphenyl-3-yl)-1H-imidazol-4-yl]-(4-methyl-pyridin-2-yl)-methanone;

[1-(2'-Methoxy-biphenyl-3-yl)-1H-imidazol-4-yl]-pyrimidin-2-yl-methanone;
(4-Fluoro-phenyl)-[1-(2'-methoxy-biphenyl-3-yl)-1H-imidazol-4-yl]-methanone;
(3-Fluoro-phenyl)-[1-(2'-methoxy-biphenyl-3-yl)-1H-imidazol-4-yl]-methanone;
(4-Methoxy-phenyl)-[1-(2'-methoxy-biphenyl-3-yl)-1H-imidazol-4-yl]-methanone;
(3-Methoxy-phenyl)-[1-(2'-methoxy-biphenyl-3-yl)-1H-imidazol-4-yl]-methanone;
(2-Methoxy-phenyl)-[1-(2'-methoxy-biphenyl-3-yl)-1H-imidazol-4-yl]-methanone;
[1-(2'-Methoxy-biphenyl-3-yl)-1H-imidazol-4-yl]-thiazol-2-yl-methanone;
[1-(2'-Methoxy-biphenyl-3-yl)-1H-imidazol-4-yl]-(5-methyl-thiazol-2-yl)-methanone;
[1-(2'-Methoxy-biphenyl-3-yl)-1H-imidazol-4-yl]-(1-methyl-imidazol-2-yl)-methanone;
Furan-2-yl-[1-(2'-methoxy-biphenyl-3-yl)-1H-imidazol-4-yl]-methanone;
3'-[4-(Pyridine-2-carbonyl)-imidazol-1-yl]-biphenyl-2-carbonitrile;
3'-[4-(3-Methyl-pyridine-2-carbonyl)-imidazol-1-yl]-biphenyl-2-carbonitrile;
3'-[4-(4-Methyl-pyridine-2-carbonyl)-imidazol-1-yl]-biphenyl-2-carbonitrile;
3'-[4-(Pyrimidine-2-carbonyl)-imidazol-1-yl]-biphenyl-2-carbonitrile;
3'-[4-(4-Fluoro-benzoyl)-imidazol-1-yl]-biphenyl-2-carbonitrile;
3'-[4-(3-Fluoro-benzoyl)-imidazol-1-yl]-biphenyl-2-carbonitrile;
3'-[4-(4-Methoxy-benzoyl)-imidazol-1-yl]-biphenyl-2-carbonitrile;
3'-[4-(3-Methoxy-benzoyl)-imidazol-1-yl]-biphenyl-2-carbonitrile;
3'-[4-(2-Methoxy-benzoyl)-imidazol-1-yl]-biphenyl-2-carbonitrile;
3'-[4-(Thiazole-2-carbonyl)-imidazol-1-yl]-biphenyl-2-carbonitrile;
3'-[4-(5-Methyl-thiazole-2-carbonyl)-imidazol-1-yl]-biphenyl-2-carbonitrile;
3'-[4-(1-Methyl-1H-imidazole-2-carbonyl)-imidazol-1-yl]-biphenyl-2-carbonitrile;
3'-[4-(Furan-2-carbonyl)-imidazol-1-yl]-biphenyl-2-carbonitrile;
[1-(2'-Chloro-biphenyl-3-yl)-1H-imidazol-4-yl]-pyridin-2-yl-methanone;
[1-(2'-Chloro-biphenyl-3-yl)-1H-imidazol-4-yl]-(3-methyl-pyridin-2-yl)-methanone;
[1-(2'-Chloro-biphenyl-3-yl)-1H-imidazol-4-yl]-(4-methyl-pyridin-2-yl)-methanone;
[1-(2'-Chloro-biphenyl-3-yl)-1H-imidazol-4-yl]-pyrimidin-2-yl-methanone;
[1-(2'-Chloro-biphenyl-3-yl)-1H-imidazol-4-yl]-(4-fluoro-phenyl)-methanone;
[1-(2'-Chloro-biphenyl-3-yl)-1H-imidazol-4-yl]-(3-fluoro-phenyl)-methanone;
[1-(2'-Chloro-biphenyl-3-yl)-1H-imidazol-4-yl]-(4-methoxy-phenyl)-methanone;
[1-(2'-Chloro-biphenyl-3-yl)-1H-imidazol-4-yl]-(3-methoxy-phenyl)-methanone;
[1-(2'-Chloro-biphenyl-3-yl)-1H-imidazol-4-yl]-(2-methoxy-phenyl)-methanone;
[1-(2'-Chloro-biphenyl-3-yl)-1H-imidazol-4-yl]-thiazol-2-yl-methanone;
[1-(2'-Chloro-biphenyl-3-yl)-1H-imidazol-4-yl]-(5-methyl-thiazol-2-yl)-methanone;
[1-(2'-Chloro-biphenyl-3-yl)-1H-imidazol-4-yl]-(1-methyl-1H-imidazol-2-yl)-methanone;
[1-(2'-Chloro-biphenyl-3-yl)-1H-imidazol-4-yl]-furan-2-yl-methanone;
Pyridin-2-yl-[1-(2'-trifluoromethoxy-biphenyl-3-yl)-1H-imidazol-4-yl]-methanone;
(3-Methyl-pyridin-2-yl)-[1-(2'-trifluoromethoxy-biphenyl-3-yl)-1H-imidazol-4-yl]-methanone;
(4-Methyl-pyridin-2-yl)-[1-(2'-trifluoromethoxy-biphenyl-3-yl)-1H-imidazol-4-yl]-methanone;
Pyrimidin-2-yl-[1-(2'-trifluoromethoxy-biphenyl-3-yl)-1H-imidazol-4-yl]-methanone;
(4-Fluoro-phenyl)-[1-(2'-trifluoromethoxy-biphenyl-3-yl)-1H-imidazol-4-yl]-methanone;
(3-Fluoro-phenyl)-[1-(2'-trifluoromethoxy-biphenyl-3-yl)-1H-imidazol-4-yl]-methanone;
(4-Methoxy-phenyl)-[1-(2'-trifluoromethoxy-biphenyl-3-yl)-1H-imidazol-4-yl]-methanone;
(3-Methoxy-phenyl)-[1-(2'-trifluoromethoxy-biphenyl-3-yl)-1H-imidazol-4-yl]-methanone;
(2-Methoxy-phenyl)-[1-(2'-trifluoromethoxy-biphenyl-3-yl)-1H-imidazol-4-yl]-methanone;
Thiazol-2-yl-[1-(2'-trifluoromethoxy-biphenyl-3-yl)-1H-imidazol-4-yl]-methanone;
(5-Methyl-thiazol-2-yl)-[1-(2'-trifluoromethoxy-biphenyl-3-yl)-1H-imidazol-4-yl]-methanone;
(1-Methyl-1H-Imidazol-2-yl)-[1-(2'-trifluoromethoxy-biphenyl-3-yl)-1H-imidazol-4-yl]-methanone;
Furan-2-yl-[1-(2'-trifluoromethoxy-biphenyl-3-yl)-1H-imidazol-4-yl]-methanone;
[1-(6'-Fluoro-2'-methoxy-biphenyl-3-yl)-1H-imidazol-4-yl]-pyridin-2-yl-methanone;
[1-(6'-Fluoro-2'-methoxy-biphenyl-3-yl)-1H-imidazol-4-yl]-(3-methyl-pyridin-2-yl)-methanone;
[1-(6'-Fluoro-2'-methoxy-biphenyl-3-yl)-1H-imidazol-4-yl]-(4-methyl-pyridin-2-yl)-methanone;
[1-(6'-Fluoro-2'-methoxy-biphenyl-3-yl)-1H-imidazol-4-yl]-pyrimidin-2-yl-methanone;
[1-(6'-Fluoro-2'-methoxy-biphenyl-3-yl)-1H-imidazol-4-yl]-(4-fluoro-phenyl)-methanone;
[1-(6'-Fluoro-2'-methoxy-biphenyl-3-yl)-1H-imidazol-4-yl]-(3-fluoro-phenyl)-methanone;
[1-(6'-Fluoro-2'-methoxy-biphenyl-3-yl)-1H-imidazol-4-yl]-(4-methoxy-phenyl)-methanone;
[1-(6'-Fluoro-2'-methoxy-biphenyl-3-yl)-1H-imidazol-4-yl]-(3-methoxy-phenyl)-methanone;
[1-(6'-Fluoro-2'-methoxy-biphenyl-3-yl)-1H-imidazol-4-yl]-(2-methoxy-phenyl)-methanone;
[1-(6'-Fluoro-2'-methoxy-biphenyl-3-yl)-1H-imidazol-4-yl]-thiazol-2-yl-methanone;
[1-(6'-Fluoro-2'-methoxy-biphenyl-3-yl)-1H-imidazol-4-yl]-(5-methyl-thiazol-2-yl)-methanone;
[1-(6'-Fluoro-2'-methoxy-biphenyl-3-yl)-1H-imidazol-4-yl]-(1-methyl-1H-imidazol-2-yl)-methanone;
[1-(6'-Fluoro-2'-methoxy-biphenyl-3-yl)-1H-imidazol-4-yl]-furan-2-yl-methanone;
[1-(3'-Fluoro-2'-methoxy-biphenyl-3-yl)-1H-imidazol-4-yl]-pyridin-2-yl-methanone;
[1-(3'-Fluoro-2'-methoxy-biphenyl-3-yl)-1H-imidazol-4-yl]-(3-methyl-pyridin-2-yl)-methanone;
[1-(3'-Fluoro-2'-methoxy-biphenyl-3-yl)-1H-imidazol-4-yl]-(4-methyl-pyridin-2-yl)-methanone;
[1-(3'-Fluoro-2'-methoxy-biphenyl-3-yl)-1H-imidazol-4-yl]-pyrimidin-2-yl-methanone;
[1-(3'-Fluoro-2'-methoxy-biphenyl-3-yl)-1H-imidazol-4- yl]-(4-fluoro-phenyl)-methanone;
[1-(3'-Fluoro-2'-methoxy-biphenyl-3-yl)-1H-imidazol-4-yl]-(3-fluoro-phenyl)-methanone;
[1-(3'-Fluoro-2'-methoxy-biphenyl-3-yl)-1H-imidazol-4-yl]-(4-methoxy-phenyl)-methanone;
[1-(3'-Fluoro-2'-methoxy-biphenyl-3-yl)-1H-imidazol-4-yl]-(3-methoxy-phenyl)-methanone;
[1-(3'-Fluoro-2'-methoxy-biphenyl-3-yl)-1H-imidazol-4-yl]-(2-methoxy-phenyl)-methanone;
[1-(3'-Fluoro-2'-methoxy-biphenyl-3-yl)-1H-imidazol-4-yl]-thiazol-2-yl-methanone;
[1-(3'-Fluoro-2'-methoxy-biphenyl-3-yl)-1H-imidazol-4-yl]-(5-methyl-thiazol-2-yl)-methanone;
[1-(3'-Fluoro-2'-methoxy-biphenyl-3-yl)-1H-imidazol-4-yl]-(1-methyl-1H-imidazol-2-yl)-methanone;
[1-(3'-Fluoro-2'-methoxy-biphenyl-3-yl)-1H-imidazol-4-yl]-furan-2-yl-methanone;
{1-[3-(2-Fluoro-pyridin-3-yl)-phenyl]-1H-imidazol-4-yl}-pyridin-2-yl-methanone;
{1-[3-(2-Fluoro-pyridin-3-yl)-phenyl]-1H-imidazol-4-yl}-(3-methyl-pyridin-2-yl)-methanone;
{1-[3-(2-Fluoro-pyridin-3-yl)-phenyl]-1H-imidazol-4-yl}-(4-methyl-pyridin-2-yl)-methanone;
{1-[3-(2-Fluoro-pyridin-3-yl)-phenyl]-1H-imidazol-4-yl}-pyrimidin-2-yl-methanone;
(4-Fluoro-phenyl)-{1-[3-(2-fluoro-pyridin-3-yl)-phenyl]-1H-imidazol-4-yl}-methanone;
(3-Fluoro-phenyl)-{1-[3-(2-fluoro-pyridin-3-yl)-phenyl]-1H-imidazol-4-yl}-methanone;
{1-[3-(2-Fluoro-pyridin-3-yl)-phenyl]-1H-imidazol-4-yl}-(4-methoxy-phenyl)-methanone;
{1-[3-(2-Fluoro-pyridin-3-yl)-phenyl]-1H-imidazol-4-yl}-(3-methoxy-phenyl)-methanone;
{1-[3-(2-Fluoro-pyridin-3-yl)-phenyl]-1H-imidazol-4-yl}-(2-methoxy-phenyl)-methanone;
{1-[3-(2-Fluoro-pyridin-3-yl)-phenyl]-1H-imidazol-4-yl}-thiazol-2-yl-methanone;
{1-[3-(2-Fluoro-pyridin-3-yl)-phenyl]-1H-imidazol-4-yl}-(5-methyl-thiazol-2-yl)-methanone;
{1-[3-(2-Fluoro-pyridin-3-yl)-phenyl]-1H-imidazol-4-yl}-(1-methyl-1H-imidazol-2-yl)-methanone;
{1-[3-(2-Fluoro-pyridin-3-yl)-phenyl]-1H-imidazol-4-yl}-furan-2-yl-methanone;
{1-[3-(2,4-Difluoro-pyridin-3-yl)-phenyl]-1H-imidazol-4-yl}-pyridin-2-yl-methanone;
{1-[3-(2,4-Difluoro-pyridin-3-yl)-phenyl]-1H-imidazol-4-yl}-(3-methyl-pyridin-2-yl)-methanone;
{1-[3-(2,4-Difluoro-pyridin-3-yl)-phenyl]-1H-imidazol-4-yl}-(4-methyl-pyridin-2-yl)-methanone;
{1-[3-(2,4-Difluoro-pyridin-3-yl)-phenyl]-1H-imidazol-4-yl}-pyrimidin-2-yl-methanone;
{1-[3-(2,4-Difluoro-pyridin-3-yl)-phenyl]-1H-imidazol-4-yl}-(4-fluoro-phenyl)-methanone;
{1-[3-(2,4-Difluoro-pyridin-3-yl)-phenyl]-1H-imidazol-4-yl}-(3-fluoro-phenyl)-methanone;
{1-[3-(2,4-Difluoro-pyridin-3-yl)-phenyl]-1H-imidazol-4-yl}-(4-methoxy-phenyl)-methanone;
{1-[3-(2,4-Difluoro-pyridin-3-yl)-phenyl]-1H-imidazol-4-yl}-(3-methoxy-phenyl)-methanone;
{1-[3-(2,4-Difluoro-pyridin-3-yl)-phenyl]-1H-imidazol-4-yl}-(2-methoxy-phenyl)-methanone;
{1-[3-(2,4-Difluoro-pyridin-3-yl)-phenyl]-1H-imidazol-4-yl}-thiazol-2-yl-methanone;
{1-[3-(2,4-Difluoro-pyridin-3-yl)-phenyl]-1H-imidazol-4-yl}-(5-methyl-thiazol-2-yl)-methanone;
{1-[3-(2,4-Difluoro-pyridin-3-yl)-phenyl]-1H-imidazol-4-yl}-(1-methyl-1H-imidazol-2-yl)-methanone;
{1-[3-(2,4-Difluoro-pyridin-3-yl)-phenyl]-1H-imidazol-4-yl}-furan-2-yl-methanone;
{1-[3-(3-Fluoro-pyridin-4-yl)-phenyl]-1H-imidazol-4-yl}-pyridin-2-yl-methanone;
{1-[3-(3-Fluoro-pyridin-4-yl)-phenyl]-1H-imidazol-4-yl}-(3-methyl-pyridin-2-yl)-methanone;
{1-[3-(3-Fluoro-pyridin-4-yl)-phenyl]-1H-imidazol-4-yl}-(4-methyl-pyridin-2-yl)-methanone;
{1-[3-(3-Fluoro-pyridin-4-yl)-phenyl]-1H-imidazol-4-yl}-pyrimidin-2-yl-methanone;
(4-Fluoro-phenyl)-{1-[3-(3-fluoro-pyridin-4-yl)-phenyl]-1H-imidazol-4-yl}-methanone;
(3-Fluoro-phenyl)-{1-[3-(3-fluoro-pyridin-4-yl)-phenyl]-1H-imidazol-4-yl}-methanone;
{1-[3-(3-Fluoro-pyridin-4-yl)-phenyl]-1H-imidazol-4-yl}-(4-methoxy-phenyl)-methanone;
{1-[3-(3-Fluoro-pyridin-4-yl)-phenyl]-1H-imidazol-4-yl}-(3-methoxy-phenyl)-methanone;
{1-[3-(3-Fluoro-pyridin-4-yl)-phenyl]-1H-imidazol-4-yl}-(2-methoxy-phenyl)-methanone;
{1-[3-(3-Fluoro-pyridin-4-yl)-phenyl]-1H-imidazol-4-yl}-thiazol-2-yl-methanone;
{1-[3-(3-Fluoro-pyridin-4-yl)-phenyl]-1H-imidazol-4-yl}-(5-methyl-thiazol-2-yl)-methanone;
{1-[3-(3-Fluoro-pyridin-4-yl)-phenyl]-1H-imidazol-4-yl}-(1-methyl-1H-imidazol-2-yl)-methanone;
{1-[3-(3-Fluoro-pyridin-4-yl)-phenyl]-1H-imidazol-4-yl}-furan-2-yl-methanone;
{1-[3-(2-Chloro-pyridin-3-yl)-phenyl]-1H-imidazol-4-yl}-pyridin-2-yl-methanone;
{1-[3-(2-Chloro-pyridin-3-yl)-phenyl]-1H-imidazol-4-yl}-(3-methyl-pyridin-2-yl)-methanone;
{1-[3-(2-Chloro-pyridin-3-yl)-phenyl]-1H-imidazol-4-yl}-(4-methyl-pyridin-2-yl)-methanone;
{1-[3-(2-Chloro-pyridin-3-yl)-phenyl]-1H-imidazol-4-yl}-pyrimidin-2-yl-methanone;
(4-Fluoro-phenyl)-{1-[3-(2-chloro-pyridin-3-yl)-phenyl]-1H-imidazol-4-yl}-methanone;
(3-Fluoro-phenyl)-{1-[3-(2-chloro-pyridin-3-yl)-phenyl]-1H-imidazol-4-yl}-methanone;
{1-[3-(2-Chloro-pyridin-3-yl)-phenyl]-1H-imidazol-4-yl}-(4-methoxy-phenyl)-methanone;
{1-[3-(2-Chloro-pyridin-3-yl)-phenyl]-1H-imidazol-4-yl}-(3-methoxy-phenyl)-methanone;
{1-[3-(2-Chloro-pyridin-3-yl)-phenyl]-1H-imidazol-4-yl}-(2-methoxy-phenyl)-methanone;
{1-[3-(2-Chloro-pyridin-3-yl)-phenyl]-1H-imidazol-4-yl}-thiazol-2-yl-methanone;
{1-[3-(2-Chloro-pyridin-3-yl)-phenyl]-1H-imidazol-4-yl}-(5-methyl-thiazol-2-yl)-methanone;
{1-[3-(2-Chloro-pyridin-3-yl)-phenyl]-1H-imidazol-4-yl}-(1-methyl-1H-imidazol-2-yl)-methanone;
{1-[3-(2-Chloro-pyridin-3-yl)-phenyl]-1H-imidazol-4-yl}-furan-2-yl-methanone;
{1-[3-(2,4-Dimethoxy-pyrimidin-5-yl)-phenyl]-1H-imidazol-4-yl}-pyridin-2-yl-methanone;
{1-[3-(2,4-Dimethoxy-pyrimidin-5-yl)-phenyl]-1H-imidazol-4-yl}-(3-methyl-pyridin-2-yl)-methanone;
{1-[3-(2,4-Dimethoxy-pyrimidin-5-yl)-phenyl]-1H-imidazol-4-yl}-(4-methyl-pyridin-2-yl)-methanone;
{1-[3-(2,4-Dimethoxy-pyrimidin-5-yl)-phenyl]-1H-imidazol-4-yl}-pyrimidin-2-yl-methanone;
{1-[3-(2,4-Dimethoxy-pyrimidin-5-yl)-phenyl]-1H-imidazol-4-yl}-(4-fluoro-phenyl)-methanone;
{1-[3-(2,4-Dimethoxy-pyrimidin-5-yl)-phenyl]-1H-imidazol-4-yl}-(3-fluoro-phenyl)-methanone;
{1-[3-(2,4-Dimethoxy-pyrimidin-5-yl)-phenyl]-1H-imidazol-4-yl}-(4-methoxy-phenyl)-methanone;
{1-[3-(2,4-Dimethoxy-pyrimidin-5-yl)-phenyl]-1H-imida-
  zol-4-yl}-(3-methoxy-phenyl)-methanone;
{1-[3-(2,4-Dimethoxy-pyrimidin-5-yl)-phenyl]-1H-imida-
  zol-4-yl}-(2-methoxy-phenyl)-methanone;
{1-[3-(2,4-Dimethoxy-pyrimidin-5-yl)-phenyl]-1H-imida-
  zol-4-yl}-thiazol-2-yl-methanone;
{1-[3-(2,4-Dimethoxy-pyrimidin-5-yl)-phenyl]-1H-imida-
  zol-4-yl}-(5-methyl-thiazol-2-yl)-methanone;
{1-[3-(2,4-Dimethoxy-pyrimidin-5-yl)-phenyl]-1H-imida-
  zol-4-yl}-(1-methyl-1H-imidazol-2-yl)-methanone;
{1-[3-(2,4-Dimethoxy-pyrimidin-5-yl)-phenyl]-1H-imida-
  zol-4-yl}-furan-2-yl-methanone;
(1-Biphenyl-3-yl-1H-imidazol-4-yl)-pyrazol-1-yl-metha-
  none (178);
[1-(5'-Fluoro-2'-methoxy-biphenyl-3-yl)-1H-imidazol-4-
  yl]-pyrazol-1-yl-methanone;
[1-(5'-Fluoro-2'-methoxy-biphenyl-3-yl)-1H-imidazol-4-
  yl]-pyrrol-1-yl-methanone;
any of its isomers or any mixture of its isomers,
or a pharmaceutically acceptable salt thereof.

Any combination of two or more of the embodiments as described above is considered within the scope of the present invention.

Definitions of Substituents

In the context of this invention halo represents fluoro, chloro, bromo or iodo.

In the context of this invention an alkyl group designates a univalent saturated, straight or branched hydrocarbon chain. The hydrocarbon chain preferably contain of from one to six carbon atoms ($C_{1-6}$-alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises of from two to six carbon atoms ($C_{2-6}$-alkenyl), including at least one double bond. In a most preferred embodiment the alkenyl group of the invention is ethenyl; 1- or 2-propenyl; 1-, 2- or 3-butenyl, or 1,3-butadienyl; 1-, 2-, 3-, 4- or 5-hexenyl, or 1,3-hexadienyl, or 1,3,5-hexatrienyl.

In the context of this invention an alkynyl group designates a carbon chain containing one or more triple bonds, including di-ynes, tri-ynes and poly-ynes. In a preferred embodiment the alkynyl group of the invention comprises of from two to six carbon atoms ($C_{2-6}$-alkynyl), including at least one triple bond. In its most preferred embodiment the alkynyl group of the invention is ethynyl; 1-, or 2-propynyl; 1-, 2-, or 3-butynyl, or 1,3-butadiynyl; 1-, 2-, 3-, 4-pentynyl, or 1,3-pentadiynyl; 1-, 2-, 3-, 4-, or 5-henynyl, or 1,3-hexadiynyl or 1,3,5-hexatriynyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

Alkoxy means O-alkyl, wherein alkyl is as defined above.

Alkoxyalkyl means alkoxy as above and alkyl as above, meaning for example, methoxymethyl.

In the context of this invention an aryl group designates a carbocyclic aromatic ring system such as phenyl, naphthyl (1-naphthyl or 2-naphthyl) or fluorenyl.

In the context of this invention a heteroaryl group designates an aromatic mono- or bicyclic heterocyclic group, which holds one or more heteroatoms in its ring structure. Preferred heteroatoms include nitrogen (N), oxygen (O), and sulphur (S).

Preferred monocyclic heteroaryl groups of the invention include aromatic 5- and 6-membered heterocyclic monocyclic groups, including for example, but not limited to, oxazolyl, isoxazolyl, thiazolyl, isothiazolyl, tetrazolyl, 1,2,4-oxadiazolyl, 1,2,5-oxadiazolyl, 1,3,4-oxadiazolyl, triazolyl, 1,2,4-thiadiazolyl, 1,2,5-thiadiazolyl, imidazolyl, pyrrolyl, pyrazolyl, furanyl, thienyl, pyridyl, pyrimidyl, pyridazinyl or pyrazinyl.

Preferred bicyclic heteroaryl groups of the invention include for example, but not limited to, indolizinyl, indolyl, isoindolyl, indazolyl, benzofuranyl, benzo[b]thienyl, benzimidazolyl, benzoxazolyl, benzoxadiazolyl, benzothiazolyl, benzo[d]isothiazolyl, purinyl, quinolinyl, isoquinolinyl, cinnolinyl, phthalazinyl, quinazolinyl, quinoxalinyl, 1,8-naphthyridinyl, pteridinyl, and indenyl.

5- to 7-membered heterocyclic rings comprising one nitrogen atom include for example, but not limited to, pyrrolidine, piperidine, homopiperidine, pyrroline, tetrahydropyridine, pyrazolidine, imidazolidine, piperazine, homopiperazine, and morpholine.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydro-chloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Examples of pharmaceutically acceptable cationic salts of a chemical compound of the invention include, without limitation, the sodium, the potassium, the calcium, the magnesium, the zinc, the aluminium, the lithium, the choline, the lysinium, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound of the invention include examples of suitable prodrugs of the substances according to the invention include compounds modified at one or more reactive or derivatizable groups of the parent compound. Of particular interest are compounds modified at a carboxyl group, a hydroxyl group, or an amino group. Examples of suitable derivatives are esters or amides.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

It will be appreciated by those skilled in the art that the compounds of the present invention may exist in different stereoisomeric forms—including enantiomers, diastereomers and cis-trans-isomers.

The invention includes all such isomers and any mixtures thereof including racemic mixtures.

Methods for the resolution of optical isomers, known to those skilled in the art may be used, and will be apparent to the average worker skilled in the art. Such methods include those discussed by J. Jaques, A. Collet, and S. Wilen in "Enantiomers, Racemates, and Resolutions", John Wiley and Sons, New York (1981).

Optical active compounds can also be prepared from optical active starting materials.

Labelled Compounds

The compounds of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radionuclide as a label. Positron emitting radionuclides are all candidates for usage. In the context of this invention the radionuclide is preferably selected from $^2$H (deuterium), $^3$H (tritium), $^{13}$C, $^{14}$C, $^{131}$I, $^{125}$I, $^{123}$I, and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

The chemical compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

The compounds of this invention may exist in unsolvated as well as in solvated forms with pharmaceutically acceptable solvents such as water, ethanol and the like. In general, the solvated forms are considered equivalent to the unsolvated forms for the purposes of this invention.

Biological Activity

Compounds of the invention are capable of modulating the $GABA_A$ receptor complex. They may be tested for their ability to bind to the $GABA_A$ receptor complex, including specific subunits thereof.

The compounds of the present invention, being ligands for the benzodiazepine binding site on $GABA_A$ receptors, are therefore of use in the treatment and/or prevention of a variety of disorders of the central nervous system. Thus in further aspect, the compounds of the invention are considered useful for the treatment, prevention or alleviation of a disease, disorder or condition responsive to modulation of the $GABA_A$ receptor complex in the central nervous system.

In a special embodiment, the compounds of the invention are considered useful for the treatment, prevention or alleviation of anxiety disorders, such as panic disorder with or without agoraphobia, agoraphobia without history of panic disorder, animal and other phobias including social phobias, obsessive-compulsive disorder, and generalized or substance-induced anxiety disorder;

stress disorders including post-traumatic and acute stress disorder;

sleep disorders;

memory disorder;

neuroses;

convulsive disorders, for example epilepsy, seizures, convulsions, or febrile convulsions in children;

migraine;

mood disorders;

depressive or bipolar disorders, for example depression, single-episode or recurrent major depressive disorder, dysthymic disorder, bipolar disorder, bipolar I and bipolar II manic disorders, and cyclothymic disorder, psychotic disorders, including schizophrenia;

neurodegeneration arising from cerebral ischemia;

attention deficit hyperactivity disorder;

pain and nociception, e.g. neuropathic pain;

emesis, including acute, delayed and anticipatory emesis, in particular emesis induced by chemotherapy or radiation;

motion sickness, post-operative nausea and vomiting;

eating disorders including anorexia nervosa and bulimia nervosa;

premenstrual syndrome;

neuralgia, e.g. trigeminal neuralgia;

muscle spasm or spasticity, e.g. in paraplegic patients;

the effects of substance abuse or dependency, including alcohol withdrawal;

cognitive disorders, such as Alzheimer's disease;

cerebral ischemia, stroke, head trauma;

tinnitus: and disorders of circadian rhythm, e.g. in subjects suffering from the effects of jet lag or shift work.

Preferably the compounds of the invention are considered useful for the treatment, prevention or alleviation of anxiety disorders, such as panic disorder with or without agoraphobia, agoraphobia without history of panic disorder, animal and other phobias including social phobias, obsessive-compulsive disorder, and generalized or substance-induced anxiety disorder.

Further, the compounds of the invention may be useful as radioligands in assays for detecting compounds capable of binding to the human $GABA_A$ receptor.

Pharmaceutical Compositions

In another aspect the invention provides novel pharmaceutical compositions comprising a therapeutically effective amount of the chemical compound of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient, which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

In another aspect the invention provides a method for the treatment, prevention or alleviation of a disease or a disorder or a condition of a living animal body, including a human, which disease, disorder or condition is responsive to modulation of the $GABA_A$ receptor complex in the central nervous system, and which method comprises administering to such a living animal body, including a human, in need thereof an effective amount of a chemical compound of the invention.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge. When administered in combination with compounds known in the art for treatment of the diseases, the dosis regimen may be reduced.

EXAMPLES

The invention is further illustrated with reference to the following examples, which are not intended to be in any way limiting to the scope of the invention as claimed.

Example 1

The Synthesis of Common Intermediate 2 is Shown in Scheme 1

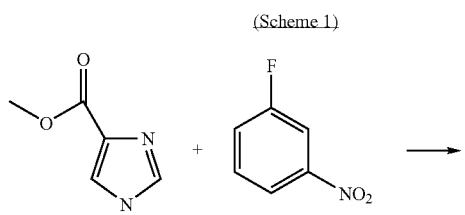

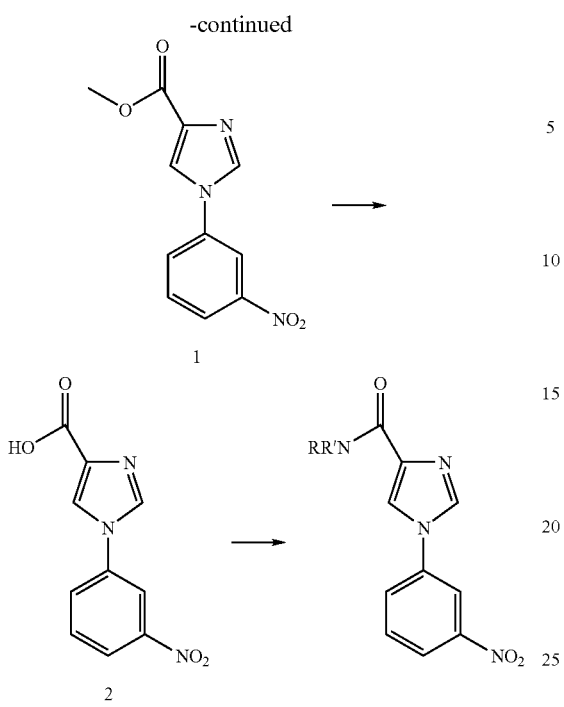

[1-(3-Nitro-phenyl)-1H-imidazole-4-carboxylic acid methyl ester] (1)

1H-Imidazole-4-carboxylic acid methyl ester (1 g, 7.9 mmol) was dissolved in MeOH and NaH (348 mg, 8.7 mmol) was added slowly. When the gas evolution had ceased 1-fluoro-3-nitro benzene (926 uL, 8.7 mmol) was added, and the mixture was heated to 150° C. under $N_2$ for 16 h. After cooling to room temperature the precipitation was isolated by suction filtration, washed with MeOH, and dried under vacuum to afford 1.3 g (67%) of 1. HRMS (ESI$^+$): m/z=247.2091 [M+H]

[1-(3-Nitro-phenyl)-1H-imidazole-4-carboxylic acid] (2)

1-(3-Nitro-phenyl)-1H-imidazole-4-carboxylic acid methyl ester 1 (0.7 g; 2.8 mmol) was suspended in MeOH (15 mL) and 2N NaOH aq. (2 mL) was added. The mixture was stirred at 70° C. for 16 h. The MeOH was evaporated and the product was isolated by suction filtration, washed with water and dried under vacuum to afford 0.56 g (86%) of 2 as an off-white solid. HRMS (ESI$^+$): m/z=233.1823 [M+H]

Amide Formation, Method A 1-(3-Nitro-phenyl)-1H-imidazole-4-carboxylic acid dimethylamide 1-(3-Nitro-phenyl)-1H-imidazole-4-carboxylic acid 2 (0.1 g, 0.4 mmol) was dissolved in DMF (5 mL) and dimethyl amine hydrochloride (33 mg, 0.4 mmol), diisopropyl amine (366 uL, 2.1 mmol), 1-hydroxy-7-azabenzotriazole (HOAt, 68 mg; 0.5 mmol) and 1-(3-dimethylaminopropyl)-3-ethyl-carbodiimide, hydrochloride (EDC HCl, 96 mg, 0.5 mmol) were added. The mixture was stirred at room temperature for 16 h. The solvent was evaporated and the residue was extracted with hot ethyl acetate. The solvent was evaporated and crystallization from MeOH afforded 30 mg (29%) pure product as white needles. HRMS (ESI$^+$): m/z=260.2518 [M+H]

1-(3-Nitro-phenyl)-1H-imidazole-4-carboxylic acid methylamide

The compound was synthesised by method A using methylamine hydrochloride. HRMS (ESI$^+$): m/z=246.225 [M+H]

1-(3-Nitro-phenyl)-1H-imidazole-4-carboxylic acid (2-hydroxy-ethyl)-amide

The compound was synthesised by method A using ethanolamine. HRMS (ESI$^+$): m/z=276.2508 [M+H]

Morpholin-4-yl-[1-(3-nitro-phenyl)-1H-imidazol-4-yl]-methanone

The compound was synthesised by method A using morpholine. HRMS (ESI$^+$): m/z=302.2886 [M+H]

1-(3-Nitro-phenyl)-1H-imidazole-4-carboxylic acid allylamide

The compound was synthesised by method A using allylamine. HRMS (ESI$^+$): m/z=272.2628 [M+H]

1-(3-Nitro-phenyl)-1H-imidazole-4-carboxylic acid propylamide

The compound was synthesised by method A using propylamine. HRMS (ESI$^+$): m/z=274.2786 [M+H]

1-(3-Nitro-phenyl)-1H-imidazole-4-carboxylic acid (2-methoxy-ethyl)-amide

The compound was synthesised by method A using 2-methoxyethyl amine. HRMS (ESI$^+$): m/z=290.2776 [M+H]

1-(3-Nitro-phenyl)-1H-imidazole-4-carboxylic acid (2-methoxy-1-methyl-ethyl)-amide The compound was synthesised by method A using 2-amino-1-methoxypropane. HRMS (ESI$^+$): m/z=304.3044 [M+H]

1-(3-Nitro-phenyl)-1H-imidazole-4-carboxylic acid (2-hydroxy-1-methyl-ethyl)-amide The compound was synthesised by method A using 2-amino-1-propanol. HRMS (ESI$^+$): m/z=290.2776 [M+H]

1-(3-Nitro-phenyl)-1H-imidazole-4-carboxylic acid isopropylamide

The compound was synthesised by method A using isopropyl amine. HRMS (ESI$^+$): m/z=274.2786 [M+H]

(4-Methyl-piperazin-1-yl)-[1-(3-nitro-phenyl)-1H-imidazol-4-yl]-methanone

The compound was synthesised by method A using N-methylpiperazine. HRMS (ESI$^+$): m/z=315.3313 [M+H]

[1-(3-Nitro-phenyl)-1H-imidazol-4-yl]-pyrrolidin-1- yl-methanone

The compound was synthesised by method A using pyrrolidine. HRMS (ESI⁺): m/z=286.2896 [M+H]

Example 2

The Synthesis Intermediate 4 is Shown in Scheme 2

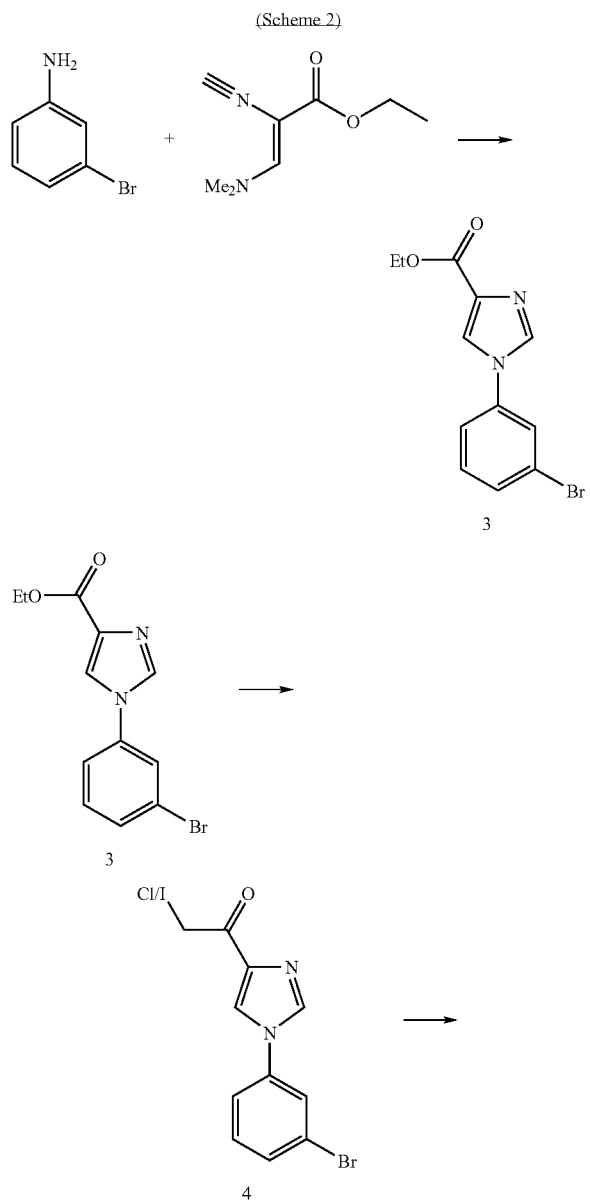

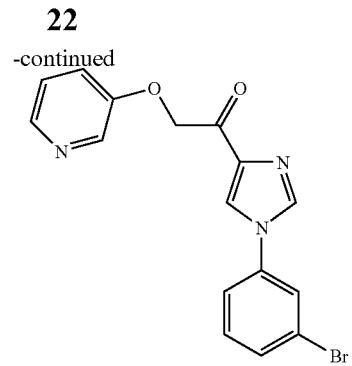

1-(3-Bromo-phenyl)-1H-imidazole-4-carboxylic acid ethyl ester (3)

A solution of compound (Z)-3-dimethylamino-2-isocyano-acrylic acid ethyl ester (11.8 g, 79 mmol) and 3-bromo aniline (11.3 g, 65 mmol) in n-butanol (90 mL) was heated to reflux for 72 h [reaction was monitored by TLC]. Reaction mixture was concentrated under reduced pressure to remove n-butanol and the residue was passed through silica gel column, eluated with a mixture of ethyl acetate and hexane to give a mixture of ethyl and n-butyl ester compounds which was then separated by flash column chromatography over silica gel using 3:7 mixture ethyl acetate and hexane as eluant. Finally the ethyl ester was further purified by crystallization to furnish 3 (2.5 g, 13%) as a brown solid. HRMS (ESI⁺): m/z=295.1349 [M+H]

1-[1-(3-Bromo-phenyl)-1H-imidazol-4-yl]-2-chloroethanone (4)

A solution of diisopropylethyl amine (1.3 mL, 9.3 mmol) in dry THF (15 mL) under argon atmosphere was added n-BuLi (2.5 M in hexanes, 3.4 mL) at −78° C. and then dropwise added over 25 min to a solution of (0.5 g; 1.7 mmol) and chloroiodo methane (0.5 mL, 6.8 mmol) in THF at −78° C. The reaction mixture was stirred for 20 min after which glacial acetic acid (2.5 mL) in THF (15 mL) was slowly added keeping the temperature <−65° C. After stirring for 15 min at this temperature the mixture was poured into water/ethyl acetate (1:1, 100 mL). The layers were separated and the organic layer was washed with saturated NaHCO₃, saturated aqueous NaCl, dried on Na₂SO₄ and concentrated. Column chromatography on silica gel with 1% MeOH in CH₂Cl₂ afforded 60 mg (12%) of 17—a mixture of α-chloro and α-iodo ketone 4 which was taken as such for the next step.

1-[1-(3-Bromo-phenyl)-1H-imidazol-4-yl]-2-(pyridin-3-yloxy)-ethanone (5)

1-[1-(3-Bromo-phenyl)-1H-imidazol-4-yl]-2-chloroethanone 4 (60 mg; 0.17 mmol) was dissolved in acetone (5 mL). 3-Hydroxypyridine (22 mg; 0.23 mmol) and K₂CO₃ (117 mg; 0.85 mmol) were added and heated to reflux for 16 h. The mixture was partitioned between EtOAc and water. The organic phase was then washed with 2N NaOH, saturated aqueous NaCl and was dried over Na₂SO₄. Concentration of the organic layer afforded 15 mg (25%) of 5. HRMS (ESI⁺): m/z=358.1938 [M+H]

Example 3

23

The Synthesis of Compounds 6, 7 and 8 is Shown in Scheme 3

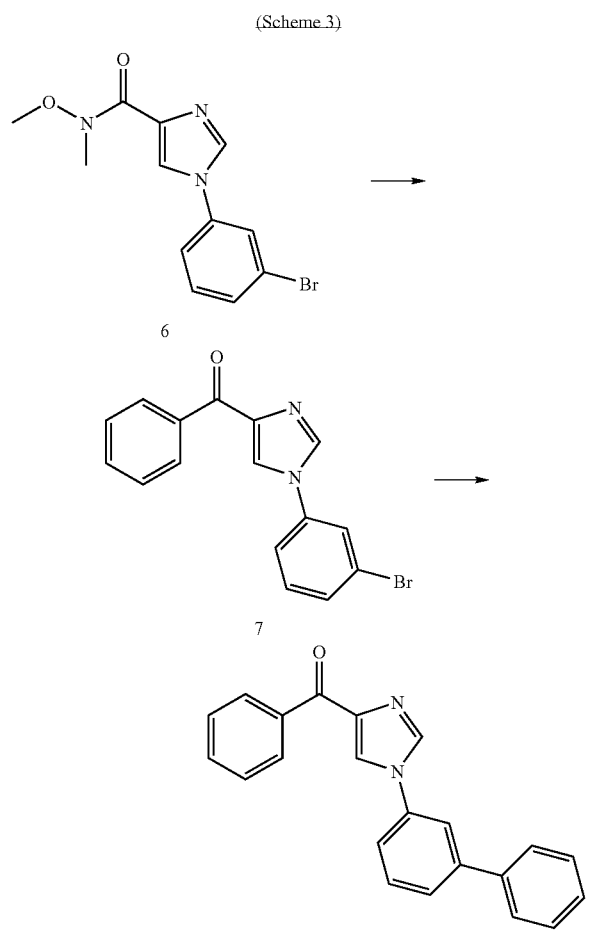

(Scheme 3)

6

7

8

1-(3-Bromo-phenyl)-1H-imidazole-4-carboxylic acid methoxy-methyl-amide (6)

The compound was synthesised by method A using 3 and N,O-dimethylhydroxyl amine.

[1-(3-Bromo-phenyl)-1H-imidazol-4-yl]-phenyl-methanone (7)

A solution of 6 [(130 mg, 0.42 mmol); in flame dried glassware and under argon atmosphere] in dry diethyl ether (15 mL) was cooled to −78° C. Phenyl magnesium bromide (1 M in THF, 1.4 mL) was added dropwise and the mixture was allowed to go to room temperature over night. The reaction mixture was quenched with 1 M NH$_4$Cl aqueous solution and stirred for 30 min. The layers were separated and the organic phase was dried over Na$_2$SO$_4$ and concentrated. Recrystallisation from isopropanol afforded 43 mg (31%) 7 as a solid. HRMS (ESI$^+$): m/z=327.1799 [M+H]

Suzuki Coupling

Method B

24

(1-Biphenyl-3-yl-1H-imidazol-4-yl)-phenyl-methanone (8)

A solution of 7 (250 mg, 0.76 mmol), phenylboronic acid (102 mg, 0.84 mmol) and Na$_2$CO$_3$ (244 mg, 2.3 mmol) in DME/H$_2$O 4:1 (10 mL) was thoroughly purged with argon, after which Pd(PPh$_3$)$_2$Cl$_2$ (36 mg; 0.05 mmol) was added and the mixture was heated to 70° C. for 21 h. The solvents were removed in vacuo and the residue was purified by column chromatography (1 to 5% methanol in CH$_2$Cl$_2$ to give 100 mg (41%) pure 8. HRMS (ESI$^+$): m/z=324.3814 [M+H]

Example 4

The Synthesis of Compounds 13-177 is Shown in Scheme 4

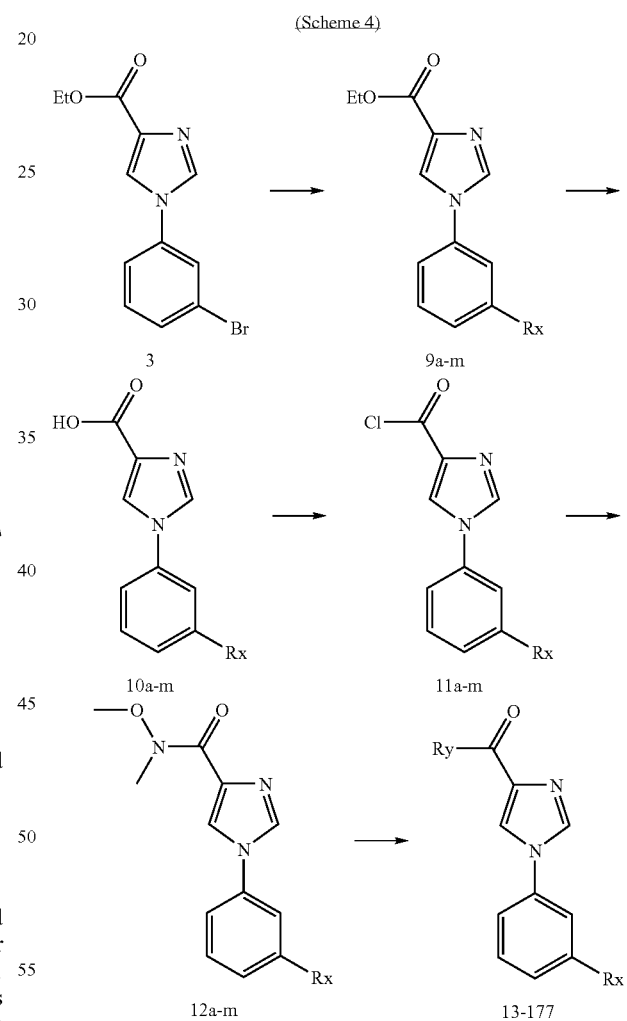

(Scheme 4)

3

9a-m 10a-m 11a-m 12a-m 13-177

1-Biphenyl-3-yl-1H-imidazole-4-carboxylic acid ethyl ester (9a)

This compound was synthesised by Method B using 3.

1-(5'-Fluoro-2'-methoxy-biphenyl-3-yl)-1H-imidazole-4-carboxylic acid ethyl ester (9b)

This compound is synthesised by Method B using 3 and 5-fluoro-2-methoxyphenylboronic acid.

1-(2'-Methoxy-biphenyl-3-yl)-1H-imidazole-4-carboxylic acid ethyl ester (9c)

This compound is synthesised by Method B using 3 and 2-methoxyphenylboronic acid.

1-(2'-Cyano-biphenyl-3-yl)-1H-imidazole-4-carboxylic acid ethyl ester (9d)

This compound is synthesised by Method B using 3 and 2-cyanophenylboronic acid.

1-(2'-Chloro-biphenyl-3-yl)-1H-imidazole-4-carboxylic acid ethyl ester (9e)

This compound is synthesised by Method B using 3 and 2-chlorophenylboronic acid.

1-(2'-Trifluoromethoxy-biphenyl-3-yl)-1H-imidazole-4-carboxylic acid ethyl ester (9f)

This compound is synthesised by Method B using 3 and 2-(trifluoromethoxy)phenyl-boronic acid.

1-(6'-Fluoro-2'-methoxy-biphenyl-3-yl)-1H-imidazole-4-carboxylic acid ethyl ester (9g)

This compound is synthesised by Method B using 3 and 6-fluoro-2-methoxyphenylboronic acid.

1-(3'-Fluoro-2'-methoxy-biphenyl-3-yl)-1H-imidazole-4-carboxylic acid ethyl ester (9h)

This compound is synthesised by Method B using 3 and 3-fluoro-2-methoxyphenyl-boronic acid.

1-[3-(2-Fluoro-pyridin-3-yl)-phenyl]-1H-imidazole-4-carboxylic acid ethyl ester (9i)

This compound is synthesised by Method B using 3 and 2-fluoro-3-pyridylboronic acid.

1-[3-(2,4-Difluoro-pyridin-3-yl)-phenyl]-1H-imidazole-4-carboxylic acid ethyl ester (9j)

This compound is synthesised by Method B using 3 and 2,4-difluoro-3-pyridylboronic acid.

1-[3-(2-Fluoro-pyridin-4-yl)-phenyl]-1H-imidazole-4-carboxylic acid ethyl ester (9k)

This compound is synthesised by Method B using 3 and 2-fluoro-4-pyridylboronic acid.

1-[3-(2-Chloro-pyridin-3-yl)-phenyl]-1H-imidazole-4-carboxylic acid ethyl ester (9l)

This compound is synthesised by Method B using 3 and 2-chloro-3-pyridylboronic acid.

1-[3-(2,4-Dimethoxy-pyrimidin-5-yl)-phenyl]-1H-imidazole-4-carboxylic acid ethyl ester (9m)

This compound is synthesised by Method B using 3 and 2,4-dimethoxy-5-pyrimidyl-boronic acid.

1-Biphenyl-3-yl-1H-imidazole-4-carboxylic acid (10a)

This compound was prepared by hydrolysis of 9a using a 1:1 mixture of aqueous potassium hydroxide (2M) and ethanol.

1-(5'-Fluoro-2'-methoxy-biphenyl-3-yl)-1H-imidazole-4-carboxylic acid (10b)

This compound was prepared by hydrolysis of 9b using a 1:1 mixture of aqueous potassium hydroxide (2M) and ethanol.

1-(2'-Methoxy-biphenyl-3-yl)-1H-imidazole-4-carboxylic acid (10c)

This compound is prepared by hydrolysis of 9c using a 1:1 mixture of aqueous potassium hydroxide (2M) and ethanol.

1-(2'-Cyano-biphenyl-3-yl)-1H-imidazole-4-carboxylic acid (10d)

This compound is prepared by hydrolysis of 9d using a 1:1 mixture of aqueous potassium hydroxide (2M) and ethanol.

1-(2'-Chloro-biphenyl-3-yl)-1H-imidazole-4-carboxylic acid (10e)

This compound is prepared by hydrolysis of 9e using a 1:1 mixture of aqueous potassium hydroxide (2M) and ethanol.

1-(2'-Trifluoromethoxy-biphenyl-3-yl)-1H-imidazole-4-carboxylic acid (10f)

This compound is prepared by hydrolysis of 9f using a 1:1 mixture of aqueous potassium hydroxide (2M) and ethanol.

1-(6'-Fluoro-2'-methoxy-biphenyl-3-yl)-1H-imidazole-4-carboxylic acid (10g)

This compound is prepared by hydrolysis of 9g using a 1:1 mixture of aqueous potassium hydroxide (2M) and ethanol.

1-(3'-Fluoro-2'-methoxy-biphenyl-3-yl)-1H-imidazole-4-carboxylic acid (10h)

This compound is prepared by hydrolysis of 9h using a 1:1 mixture of aqueous potassium hydroxide (2M) and ethanol.

1-[3-(2-Fluoro-pyridin-3-yl)-phenyl]-1H-imidazole-4-carboxylic acid (10i)

This compound is prepared by hydrolysis of 9i using a 1:1 mixture of aqueous potassium hydroxide (2M) and ethanol.

1-[3-(2,4-Difluoro-pyridin-3-yl)-phenyl]-1H-imidazole-4-carboxylic acid (10j)

This compound is prepared by hydrolysis of 9j using a 1:1 mixture of aqueous potassium hydroxide (2M) and ethanol.

1-[3-(2-Fluoro-pyridin-4-yl)-phenyl]-1H-imidazole-4-carboxylic acid (10k)

This compound is prepared by hydrolysis of 9k using a 1:1 mixture of aqueous potassium hydroxide (2M) and ethanol.

1-[3-(2-Chloro-pyridin-3-yl)-phenyl]-1H-imidazole-4-carboxylic acid (10l)

This compound is prepared by hydrolysis of 9l using a 1:1 mixture of aqueous potassium hydroxide (2M) and ethanol.

1-[3-(2,4-Dimethoxy-pyrimidin-5-yl)-phenyl]-1H-imidazole-4-carboxylic acid (10m)

This compound is prepared by hydrolysis of 9m using a 1:1 mixture of aqueous potassium hydroxide (2M) and ethanol.

1-Biphenyl-3-yl-1H-imidazole-4-carbonyl chloride (11a)

A solution of 10a (2.0 g, 7.6 mmol) in oxalyl chloride (30 ml) was stirred at 60° C. overnight. Excess oxalyl chloride was removed under reduced pressure to leave 11a.

1-(5'-Fluoro-2'-methoxy-biphenyl-3-yl)-1H-imidazole-4-carbonyl chloride (11b)

This compound was prepared analogously to 11a from 10b.

1-(2'-Methoxy-biphenyl-3-yl)-1H-imidazole-4-carbonyl chloride (11c)

This compound is prepared analogously to 11a from 10c.

1-(2'-Cyano-biphenyl-3-yl)-1H-imidazole-4-carbonyl chloride (11d)

This compound is prepared analogously to 11a from 10d.

1-(2'-Chloro-biphenyl-3-yl)-1H-imidazole-4-carbonyl chloride (11e)

This compound is prepared analogously to 11a from 10e.

1-(2'-Trifluoromethoxy-biphenyl-3-yl)-1H-imidazole-4-carbonyl chloride (11f)

This compound is prepared analogously to 11a from 10f.

1-(6'-Fluoro-2'-methoxy-biphenyl-3-yl)-1H-imidazole-4-carbonyl chloride (11g)

This compound is prepared analogously to 11a from 10g.

1-(3'-Fluoro-2'-methoxy-biphenyl-3-yl)-1H-imidazole-4-carbonyl chloride (11h)

This compound is prepared analogously to 11a from 10h.

1-[3-(2-Fluoro-pyridin-3-yl)-phenyl]-1H-imidazole-4-carbonyl chloride (11i)

This compound is prepared analogously to 11a from 10i.

1-[3-(2,4-Difluoro-pyridin-3-yl)-phenyl]-1H-imidazole-4-carbonyl chloride (11j)

This compound is prepared analogously to 11a from 10j.

1-[3-(2-Fluoro-pyridin-4-yl)-phenyl]-1H-imidazole-4-carbonyl chloride (11k)

This compound is prepared analogously to 11a from 10k.

1-[3-(2-Chloro-pyridin-3-yl)-phenyl]-1H-imidazole-4-carbonyl chloride (11l)

This compound is prepared analogously to 11a from 10l.

1-[3-(2,4-Dimethoxy-pyrimidin-5-yl)-phenyl]-1H-imidazole-4-carbonyl chloride (11m)

This compound is prepared analogously to 11a from 10m.

1-Biphenyl-3-yl-1H-imidazole-4-carboxylic acid methoxy-methyl-amide (12a)

The above product (11a) was dissolved in dichloromethane (20 ml). Triethylamine (10 ml) and N,O-dimethylhydroxylamine hydrochloride (0.83 g, 8.3 mmol) were added and the resultant mixture was stirred at ambient conditions overnight. The reaction mixture was concentrated under reduced pressure and the concentrate was purified by column chromatography on silica gel using a mixture of 0.8% methanol in chloroform as the eluent to afford 12a (1.2 g).

1-(5'-Fluoro-2'-methoxy-biphenyl-3-yl)-1H-imidazole-4-carboxylic acid methoxy-methyl-amide (12b)

This compound was prepared analogously to 12a from 11b.

1-(2'-Methoxy-biphenyl-3-yl)-1H-imidazole-4-carboxylic acid methoxy-methyl-amide (12c)

This compound is prepared analogously to 12a from 11c.

1-(2'-Cyano-biphenyl-3-yl)-1H-imidazole-4-carboxylic acid methoxy-methyl-amide (12d)

This compound is prepared analogously to 12a from 11d.

1-(2'-Chloro-biphenyl-3-yl)-1H-imidazole-4-carboxylic acid methoxy-methyl-amide (12e)

This compound is prepared analogously to 12a from 11e.

1-(2'-Trifluoromethoxy-biphenyl-3-yl)-1H-imidazole-4-carboxylic acid methoxy-methyl-amide (12f)

This compound is prepared analogously to 12a from 11f.

1-(6'-Fluoro-2'-methoxy-biphenyl-3-yl)-1H-imidazole-4-carboxylic acid methoxy-methyl-amide (12g)

This compound is prepared analogously to 12a from 11g.

1-(3'-Fluoro-2'-methoxy-biphenyl-3-yl)-1H-imidazole-4-carboxylic acid methoxy-methyl-amide (12h)

This compound is prepared analogously to 12a from 11h.

1-[3-(2-Fluoro-pyridin-3-yl)-phenyl]-1H-imidazole-4-carboxylic acid methoxy-methyl-amide (12i)

This compound is prepared analogously to 12a from 11i.

1-[3-(2,4-Difluoro-pyridin-3-yl)-phenyl]-1H-imidazole-4-carboxylic acid methoxy-methyl-amide (12j)

This compound is prepared analogously to 12a from 11j.

1-[3-(2-Fluoro-pyridin-4-yl)-phenyl]-1H-imidazole- 4-carboxylic acid methoxy-methyl-amide (12k)

This compound is prepared analogously to 12a from 11k.

1-[3-(2-Chloro-pyridin-3-yl)-phenyl]-1H-imidazole-4-carboxylic acid methoxy-methyl-amide (12l)

This compound is prepared analogously to 12a from 11l.

1-[3-(2,4-Dimethoxy-pyrimidin-5-yl)-phenyl]-1H-imidazole-4-carboxylic acid methoxy-methyl-amide (12m)

This compound is prepared analogously to 12a from 11m.

Ketone Formation

Method C

Compounds 13-177 were prepared from the corresponding Weinreb amides by reaction with an arylithium moiety, generated from either an arylhalogenide or a heteroaromate upon treatment with butyllithium. Column chromatographic work-up was applied. An illustrative example is described below.

(1-Biphenyl-3-yl-1H-imidazol-4-yl)-pyridin-2-yl-methanone (13)

A solution of 2-bromopyridine (1.0 g, 6.5 mmol) in THF (20 ml) was stirred at −78° C. in a nitrogen atmosphere. n-Butyllithium (8.1 ml 1.6M solution in hexanes, 13.0 mmol) was added and stirring at −78° C. was continued for 45 min. The resultant mixture was allowed to warm to 0° C. for two hours, in order to ensure completion of anion formation. The mixture was again cooled to −78° C. and compound 12a (0.5 g, 1.6 mmol) was added. After 30 min. the mixture was allowed to warm to 0° C. and saturated, aqueous ammonium chloride was added. The mixture was extracted with ethyl acetate. The combined extracts were dried over magnesium sulfate and concentrated under reduced pressure. The concentrate was purified by column chromatography on silica gel using a mixture of petroleum ether and ethyl acetate (9:1) as the eluent. This afforded the desired product (0.15 g, 22%) as a yellowish gum. HRMS (ESI$^+$): m/z=326.1305 [M+H]

[1-(5'-Fluoro-2'-methoxy-biphenyl-3-yl)-1H-imidazol-4-yl]-pyridin-2-yl-methanone (14)

This compound was prepared by Method C using compound 12b. HRMS (ESI$^+$): m/z=374.1311 [M+H]

[1-(5'-Fluoro-2'-methoxy-biphenyl-3-yl)-1H-imidazol-4-yl]-(3-methyl-pyridin-2-yl)-methanone (15)

This compound was prepared by Method C using compound 12b and 2-bromo-3-methylpyridine. HRMS (ESI$^+$): m/z=388.1471 [M+H]

[1-(5'-Fluoro-2'-methoxy-biphenyl-3-yl)-1H-imidazol-4-yl]-(4-methyl-pyridin-2-yl)-methanone (16)

This compound was prepared by method C using compound 12b and 2-bromo-4-methylpyridine. HRMS (ESI$^+$): m/z=388.1481 [M+H]

[1-(5'-Fluoro-2'-methoxy-biphenyl-3-yl)-1H-imidazol-4-yl]-pyrimidin-2-yl-methanone (17)

This compound was prepared by method C using compound 12b and 2-bromopyrimidine. HRMS (ESI$^+$): m/z=375.1249 [M+H]

(1-Biphenyl-3-yl-1H-imidazol-4-yl)-(4-fluoro-phenyl)-methanone (18)

This compound was prepared by method C using compound 12a and 1-bromo-4-fluorobenzene. HRMS (ESI$^+$): m/z=343.1258 [M+H]

(1-Biphenyl-3-yl-1H-imidazol-4-yl)-(3-fluoro-phenyl)-methanone (19)

This compound was prepared by method C using compound 12a and 1-bromo-3-fluorobenzene. HRMS (ESI$^+$): m/z=343.1231 [M+H]

(1-Biphenyl-3-yl-1H-imidazol-4-yl)-(4-methoxy-phenyl)-methanone (20)

This compound was prepared by method C using compound 12a and 4-bromoanisole. HRMS (ESI$^+$): m/z=355.1456 [M+H]

(1-Biphenyl-3-yl-1H-imidazol-4-yl)-(3-methoxy-phenyl)-methanone (21) and 1-(1-Biphenyl-3-yl-1H-imidazol-4-yl)-pentan-1-one (22)

Compound 21 was prepared by method C using compound 12a and 3-bromoanisole. HRMS (ESI$^+$): m/z=355.1434 [M+H]. Compound 22 was formed as a by-product during this synthesis. HRMS (ESI$^+$): m/z=305.1642 [M+H]

(1-Biphenyl-3-yl-1H-imidazol-4-yl)-(2-methoxy-phenyl)-methanone (23)

This compound was prepared by method C using compound 12a and 2-bromoanisole. HRMS (ESI$^+$): m/z=355.1459 [M+H]

(1-Biphenyl-3-yl-1H-imidazol-4-yl)-thiazol-2-yl-methanone (24)

This compound was prepared by method C using compound 12a and thiazole. HRMS (ESI$^+$): m/z=332.0853 [M+H]

(1-Biphenyl-3-yl-1H-imidazol-4-yl)-furan-2-yl-methanone (25)

This compound was prepared by method C using compound 12a and furan. HRMS (ESI$^+$): m/z=315.1138 [M+H]

[1-(5'-Fluoro-2'-methoxy-biphenyl-3-yl)-1H-imidazol-4-yl]-thiazol-2-yl-methanone (26)

This compound was prepared by method C using compound 12b and thiazole.

[1-(5'-Fluoro-2'-methoxy-biphenyl-3-yl)-1H-imidazol-4-yl]-furan-2-yl-methanone (27)

This compound was prepared by method C using compound 12b and furan.

[1-(5'-Fluoro-2'-methoxy-biphenyl-3-yl)-1H-imidazol-4-yl]-(5-methyl-thiazol-2-yl)-methanone (28)

This compound was prepared by method C using compound 12b and 5-methylthiazole.

[1-(5'-Fluoro-2'-methoxy-biphenyl-3-yl)-1H-imidazol-4-yl]-(1-methyl-imidazol-2-yl)-methanone (29)

This compound was prepared by method C using compound 12b and 1-methylimidazole.

(1-Ethoxymethyl-1H-imidazol-2-yl)-[1-(5'-fluoro-2'-methoxy-biphenyl-3-yl)-1H-imidazol-4-yl]-methanone (30)

This compound is prepared by method C using compound 12b and 1-(ethoxymethyl)imidazole.

Deprotection of the above product followed by alkylation with the appropriate alkylation agents under standard conditions affords:

(1-Ethyl-1H-imidazol-2-yl)-[1-(5'-fluoro-2'-methoxy-biphenyl-3-yl)-1H-imidazol-4-yl]-methanone (31)

(1-i-Propyl-1H-imidazol-2-yl)-[1-(5'-fluoro-2'-methoxy-biphenyl-3-yl)-1H-imidazol-4-yl]-methanone (32)

(1-(2-Hydroxyethyl)-1H-imidazol-2-yl)-[1-(5'-fluoro-2'-methoxy-biphenyl-3-yl)-1H-imidazol-4-yl]-methanone (33)

(1-(2-Methoxyethyl)-1H-imidazol-2-yl)-[1-(5'-fluoro-2'-methoxy-biphenyl-3-yl)-1H-imidazol-4-yl]-methanone (34)

[1-(2'-Methoxy-biphenyl-3-yl)-1H-imidazol-4-yl]-pyridin-2-yl-methanone (35)

This compound is prepared by method C using compound 12c and 2-bromopyridine

[1-(2'-Methoxy-biphenyl-3-yl)-1H-imidazol-4-yl]-(3-methyl-pyridin-2-yl)-methanone (36)

This compound is prepared by method C using compound 12c and 2-bromo-3-methylpyridine

[1-(2'-Methoxy-biphenyl-3-yl)-1H-imidazol-4-yl]-(4-methyl-pyridin-2-yl)-methanone (37)

This compound is prepared by method C using compound 12c and 2-bromo-4-methylpyridine

[1-(2'-Methoxy-biphenyl-3-yl)-1H-imidazol-4-yl]-pyrimidin-2-yl-methanone (38)

This compound is prepared by method C using compound 12c and 2-bromopyrimidine (4-Fluoro-phenyl)-[1-(2'-methoxy-biphenyl-3-yl)-1H-imidazol-4-yl]-methanone (39)

This compound is prepared by method C using compound 12c and 1-bromo-4-fluorobenzene (3-Fluoro-phenyl)-[1-(2'-methoxy-biphenyl-3-yl)-1H-imidazol-4-yl]-methanone (40)

This compound is prepared by method C using compound 12c and 1-bromo-3-fluorobenzene (4-Methoxy-phenyl)-[1-(2'-methoxy-biphenyl-3-yl)-1H-imidazol-4-yl]-methanone (41)

This compound is prepared by method C using compound 12c and 4-bromoanisole (3-Methoxy-phenyl)-[1-(2'-methoxy-biphenyl-3-yl)-1H-imidazol-4-yl]-methanone (42)

This compound is prepared by method C using compound 12c and 3-bromoanisole (2-Methoxy-phenyl)-[1-(2'-methoxy-biphenyl-3-yl)-1H-imidazol-4-yl]-methanone (43)

This compound is prepared by method C using compound 12c and 2-bromoanisole

[1-(2'-Methoxy-biphenyl-3-yl)-1H-imidazol-4-yl]-thiazol-2-yl-methanone (44)

This compound is prepared by method C using compound 12c and thiazole

[1-(2'-Methoxy-biphenyl-3-yl)-1H-imidazol-4-yl]-(5-methyl-thiazol-2-yl)-methanone (45)

This compound is prepared by method C using compound 12c and 5-methylthiazole

[1-(2'-Methoxy-biphenyl-3-yl)-1H-imidazol-4-yl]-(1-methyl-imidazol-2-yl)-methanone (46)

This compound is prepared by method C using compound 12c and 1-methylimidazole

Furan-2-yl-[1-(2'-methoxy-biphenyl-3-yl)-1H-imidazol-4-yl]-methanone (47)

This compound is prepared by method C using compound 12c and furane

3'-[4-(Pyridine-2-carbonyl)-imidazol-1-yl]-biphenyl-2-carbonitrile (48)

This compound is prepared by method C using compound 12d and 2-bromopyridine.

3'-[4-(3-Methyl-pyridine-2-carbonyl)-imidazol-1-yl]-biphenyl-2-carbonitrile (49)

This compound is prepared by method C using compound 12d and 2-bromo-3-methylpyridine.

3'-[4-(4-Methyl-pyridine-2-carbonyl)-imidazol-1-yl]-biphenyl-2-carbonitrile (50)

This compound is prepared by method C using compound 12d and 2-bromo-4-methylpyridine.

3'-[4-(Pyrimidine-2-carbonyl)-imidazol-1-yl]-biphenyl-2-carbonitrile (51)

This compound is prepared by method C using compound 12d and 2-bromopyrimidine.

3'-[4-(4-Fluoro-benzoyl)-imidazol-1-yl]-biphenyl-2-carbonitrile (52)

This compound is prepared by method C using compound 12d and 1-bromo-4-fluorobenzene.

3'-[4-(3-Fluoro-benzoyl)-imidazol-1-yl]-biphenyl-2-carbonitrile (53)

This compound is prepared by method C using compound 12d and 1-bromo-3-fluorobenzene.

3'-[4-(4-Methoxy-benzoyl)-imidazol-1-yl]-biphenyl-2-carbonitrile (54)

This compound is prepared by method C using compound 12d and 4-bromoanisole.

3'-[4-(3-Methoxy-benzoyl)-imidazol-1-yl]-biphenyl-2-carbonitrile (55)

This compound is prepared by method C using compound 12d and 3-bromoanisole.

3'-[4-(2-Methoxy-benzoyl)-imidazol-1-yl]-biphenyl-2-carbonitrile (56)

This compound is prepared by method C using compound 12d and 2-bromoanisole.

3'-[4-(Thiazole-2-carbonyl)-imidazol-1-yl]-biphenyl-2-carbonitrile (57)

This compound is prepared by method C using compound 12d and thiazole.

3'-[4-(5-Methyl-thiazole-2-carbonyl)-imidazol-1-yl]-biphenyl-2-carbonitrile (58)

This compound is prepared by method C using compound 12d and 5-methylthiazole

3'-[4-(1-Methyl-1H-imidazole-2-carbonyl)-imidazol-1-yl]-biphenyl-2-carbonitrile (59)

This compound is prepared by method C using compound 12d and 1-methylimidazole

3'-[4-(Furan-2-carbonyl)-imidazol-1-yl]-biphenyl-2-carbonitrile (60)

This compound is prepared by method C using compound 12d and furane

[1-(2'-Chloro-biphenyl-3-yl)-1H-imidazol-4-yl]-pyridin-2-yl-methanone (61)

This compound is prepared by method C using compound 12e and 2-bromopyridine

[1-(2'-Chloro-biphenyl-3-yl)-1H-imidazol-4-yl]-(3-methyl-pyridin-2-yl)-methanone (62)

This compound is prepared by method C using compound 12e and 2-bromo-3-methylpyridine

[1-(2'-Chloro-biphenyl-3-yl)-1H-imidazol-4-yl]-(4-methyl-pyridin-2-yl)-methanone (63)

This compound is prepared by method C using compound 12e and 2-bromo-4-methylpyridine

[1-(2'-Chloro-biphenyl-3-yl)-1H-imidazol-4-yl]-pyrimidin-2-yl-methanone (64)

This compound is prepared by method C using compound 12e and 2-bromopyrimidine

[1-(2'-Chloro-biphenyl-3-yl)-1H-imidazol-4-yl]-(4-fluoro-phenyl)-methanone (65)

This compound is prepared by method C using compound 12e and 1-bromo-4-fluorobenzene

[1-(2'-Chloro-biphenyl-3-yl)-1H-imidazol-4-yl]-(3-fluoro-phenyl)-methanone (66)

This compound is prepared by method C using compound 12e and 1-bromo-3-fluorobenzene

[1-(2'-Chloro-biphenyl-3-yl)-1H-imidazol-4-yl]-(4-methoxy-phenyl)-methanone (67)

This compound is prepared by method C using compound 12e and 4-bromoanisole

[1-(2'-Chloro-biphenyl-3-yl)-1H-imidazol-4-yl]-(3-methoxy-phenyl)-methanone (68)

This compound is prepared by method C using compound 12e and 3-bromoanisole

[1-(2'-Chloro-biphenyl-3-yl)-1H-imidazol-4-yl]-(2-methoxy-phenyl)-methanone (69)

This compound is prepared by method C using compound 12e and 2-bromoanisole

[1-(2'-Chloro-biphenyl-3-yl)-1H-imidazol-4-yl]-thiazol-2-yl-methanone (70)

This compound is prepared by method C using compound 12e and thiazole

[1-(2'-Chloro-biphenyl-3-yl)-1H-imidazol-4-yl]-(5-methyl-thiazol-2-yl)-methanone (71)

This compound is prepared by method C using compound 12e and 5-methylthiazole

[1-(2'-Chloro-biphenyl-3-yl)-1H-imidazol-4-yl]-(1-methyl-1H-imidazol-2-yl)-methanone (72)

This compound is prepared by method C using compound 12e and 1-methylimidazole

[1-(2'-Chloro-biphenyl-3-yl)-1H-imidazol-4-yl]-furan-2-yl-methanone (73)

This compound is prepared by method C using compound 12e and furane

Pyridin-2-yl-[1-(2'-trifluoromethoxy-biphenyl-3-yl)-1H-imidazol-4-yl]-methanone (74)

This compound is prepared by method C using compound 12f and 2-bromopyridine (3-Methyl-pyridin-2-yl)-[1-(2'-trifluoromethoxy-biphenyl-3-yl)-1H-imidazol-4-yl]-methanone (75)

This compound is prepared by method C using compound 12f and 2-bromo-3-methylpyridine (4-Methyl-pyridin-2-yl)-[1-(2'-trifluoromethoxy-biphenyl-3-yl)-1H-imidazol-4-yl]-methanone (76)

This compound is prepared by method C using compound 12f and 2-bromo-4-methylpyridine Pyrimidin-2-yl-[1-(2'-trifluoromethoxy-biphenyl-3-yl)-1H-imidazol-4-yl]-methanone (77)

This compound is prepared by method C using compound 12f and 2-bromo-pyrimidine (4-Fluoro-phenyl)-[1-(2'-trifluoromethoxy-biphenyl-3-yl)-1H-imidazol-4-yl]-methanone (78)

This compound is prepared by method C using compound 12f and 1-bromo-4-fluorobenzene (3-Fluoro-phenyl)-[1-(2'-trifluoromethoxy-biphenyl-3-yl)-1H-imidazol-4-yl]-methanone (79)

This compound is prepared by method C using compound 12f and 1-bromo-3-fluorobenzene (4-Methoxy-phenyl)-[1-(2'-trifluoromethoxy-biphenyl-3-yl)-1H-imidazol-4-yl]-methanone (80)

This compound is prepared by method C using compound 12f and 4-bromoanisole (3-Methoxy-phenyl)-[1-(2'-trifluoromethoxy-biphenyl-3-yl)-1H-imidazol-4-yl]-methanone (81)

This compound is prepared by method C using compound 12f and 3-bromoanisole (2-Methoxy-phenyl)-[1-(2'-trifluoromethoxy-biphenyl-3-yl)-1H-imidazol-4-yl]-methanone (82)

This compound is prepared by method C using compound 12f and 2-bromoanisole

Thiazol-2-yl-[1-(2'-trifluoromethoxy-biphenyl-3-yl)-1H-imidazol-4-yl]-methanone (83)

This compound is prepared by method C using compound 12f and thiazole (5-Methyl-thiazol-2-yl)-[1-(2'-trifluoromethoxy-biphenyl-3-yl)-1H-imidazol-4-yl]-methanone (84)

This compound is prepared by method C using compound 12f and 5-methylthiazole (1-Methyl-1H-Imidazol-2-yl)-[1-(2'-trifluoromethoxy-biphenyl-3-yl)-1H-imidazol-4-yl]-methanone (85)

This compound is prepared by method C using compound 12f and 1-methylimidazole

Furan-2-yl-[1-(2'-trifluoromethoxy-biphenyl-3-yl)-1H-imidazol-4-yl]-methanone (86)

This compound is prepared by method C using compound 12f and furane

[1-(6'-Fluoro-2'-methoxy-biphenyl-3-yl)-1H-imidazol-4-yl]-pyridin-2-yl-methanone (87)

This compound is prepared by method C using compound 12g and 2-bromopyridine

[1-(6'-Fluoro-2'-methoxy-biphenyl-3-yl)-1H-imidazol-4-yl]-(3-methyl-pyridin-2-yl)-methanone (88)

This compound is prepared by method C using compound 12g and 2-bromo-3-methylpyridine

[1-(6'-Fluoro-2'-methoxy-biphenyl-3-yl)-1H-imidazol-4-yl]-(4-methyl-pyridin-2-yl)-methanone (89)

This compound is prepared by method C using compound 12g and 2-bromo-4-methylpyridine

[1-(6'-Fluoro-2'-methoxy-biphenyl-3-yl)-1H-imidazol-4-yl]-pyrimidin-2-yl-methanone (90)

This compound is prepared by method C using compound 12g and 2-bromopyrimidine

[1-(6'-Fluoro-2'-methoxy-biphenyl-3-yl)-1H-imidazol-4-yl]-(4-fluoro-phenyl)-methanone (91)

This compound is prepared by method C using compound 12g and 1-bromo-4-fluorobenzene

[1-(6'-Fluoro-2'-methoxy-biphenyl-3-yl)-1H-imidazol-4-yl]-(3-fluoro-phenyl)-methanone (92)

This compound is prepared by method C using compound 12g and 1-bromo-3-fluorobenzene

[1-(6'-Fluoro-2'-methoxy-biphenyl-3-yl)-1H-imidazol-4-yl]-(4-methoxy-phenyl)-methanone (93)

This compound is prepared by method C using compound 12g and 4-bromoanisole

[1-(6'-Fluoro-2'-methoxy-biphenyl-3-yl)-1H-imidazol-4-yl]-(3-methoxy-phenyl)-methanone (94)

This compound is prepared by method C using compound 12g and 3-bromoanisole

[1-(6'-Fluoro-2'-methoxy-biphenyl-3-yl)-1H-imidazol-4-yl]-(2-methoxy-phenyl)-methanone (95)

This compound is prepared by method C using compound 12g and 2-bromoanisole

[1-(6'-Fluoro-2'-methoxy-biphenyl-3-yl)-1H-imidazol-4-yl]-thiazol-2-yl-methanone (96)

This compound is prepared by method C using compound 12g and thiazole

[1-(6'-Fluoro-2'-methoxy-biphenyl-3-yl)-1H-imidazol-4-yl]-(5-methyl-thiazol-2-yl)-methanone (97)

This compound is prepared by method C using compound 12g and 5-methylthiazole

[1-(6'-Fluoro-2'-methoxy-biphenyl-3-yl)-1H-imidazol-4-yl]-(1-methyl-1H-imidazol-2-yl)-methanone (98)

This compound is prepared by method C using compound 12g and 1-methylimidazole.

[1-(6'-Fluoro-2'-methoxy-biphenyl-3-yl)-1H-imidazol-4-yl]-furan-2-yl-methanone (99)

This compound is prepared by method C using compound 12g and furane

[1-(3'-Fluoro-2'-methoxy-biphenyl-3-yl)-1H-imidazol-4-yl]-pyridin-2-yl-methanone (100)

This compound is prepared by method C using compound 12h and 2-bromopyridine

[1-(3'-Fluoro-2'-methoxy-biphenyl-3-yl)-1H-imidazol-4-yl]-(3-methyl-pyridin-2-yl)-methanone (101)

This compound is prepared by method C using compound 12h and 2-bromo-3-methylpyridine

[1-(3'-Fluoro-2'-methoxy-biphenyl-3-yl)-1H-imidazol-4-yl]-(4-methyl-pyridin-2-yl)-methanone (102)

This compound is prepared by method C using compound 12h and 2-bromo-4-methylpyridine

[1-(3'-Fluoro-2'-methoxy-biphenyl-3-yl)-1H-imidazol-4-yl]-pyrimidin-2-yl-methanone (103)

This compound is prepared by method C using compound 12h and 2-bromopyrimidine

[1-(3'-Fluoro-2'-methoxy-biphenyl-3-yl)-1H-imidazol-4-yl]-(4-fluoro-phenyl)-methanone (104)

This compound is prepared by method C using compound 12h and 1-bromo-4-fluorobenzene

[1-(3'-Fluoro-2'-methoxy-biphenyl-3-yl)-1H-imidazol-4-yl]-(3-fluoro-phenyl)-methanone (105)

This compound is prepared by method C using compound 12h and 1-bromo-3-fluorobenzene

[1-(3'-Fluoro-2'-methoxy-biphenyl-3-yl)-1H-imidazol-4-yl]-(4-methoxy-phenyl)-methanone (106)

This compound is prepared by method C using compound 12h and 4-bromoanisole

[1-(3'-Fluoro-2'-methoxy-biphenyl-3-yl)-1H-imidazol-4-yl]-(3-methoxy-phenyl)-methanone (107)

This compound is prepared by method C using compound 12h and 3-bromoanisole

[1-(3'-Fluoro-2'-methoxy-biphenyl-3-yl)-1H-imidazol-4-yl]-(2-methoxy-phenyl)-methanone (108)

This compound is prepared by method C using compound 12h and 2-bromoanisole

[1-(3'-Fluoro-2'-methoxy-biphenyl-3-yl)-1H-imidazol-4-yl]-thiazol-2-yl-methanone (109)

This compound is prepared by method C using compound 12h and thiazole

[1-(3'-Fluoro-2'-methoxy-biphenyl-3-yl)-1H-imidazol-4-yl]-(5-methyl-thiazol-2-yl)-methanone (110)

This compound is prepared by method C using compound 12h and 5-methylthiazole

[1-(3'-Fluoro-2'-methoxy-biphenyl-3-yl)-1H-imidazol-4-yl]-(1-methyl-1H-imidazol-2-yl)-methanone (111)

This compound is prepared by method C using compound 12h and 1-methylimidazole

[1-(3'-Fluoro-2'-methoxy-biphenyl-3-yl)-1H-imidazol-4-yl]-furan-2-yl-methanone (112)

This compound is prepared by method C using compound 12h and furane

{1-[3-(2-Fluoro-pyridin-3-yl)-phenyl]-1H-imidazol-4-yl}-pyridin-2-yl-methanone (113)

This compound is prepared by method C using compound 12i and 2-bromopyridine

{1-[3-(2-Fluoro-pyridin-3-yl)-phenyl]-1H-imidazol-4-yl}-(3-methyl-pyridin-2-yl)-methanone (114)

This compound is prepared by method C using compound 12i and 2-bromo-3-methylpyridine {1-[3-(2-Fluoro-pyridin-3-yl)-phenyl]-1H-imidazol-4-yl}-(4-methyl-pyridin-2-yl)-methanone (115)

This compound is prepared by method C using compound 12i and 2-bromo-4-methylpyridine {1-[3-(2-Fluoro-pyridin-3-yl)-phenyl]-1H-imidazol-4-yl}-pyrimidin-2-yl-methanone (116)

This compound is prepared by method C using compound 12i and 2-bromopyrimidine (4-Fluoro-phenyl)-{1-[3-(2-fluoro-pyridin-3-yl)-phenyl]-1H-imidazol-4-yl}-methanone (117)

This compound is prepared by method C using compound 12i and 1-bromo-4-fluorobenzene (3-Fluoro-phenyl)-{1-[3-(2-fluoro-pyridin-3-yl)-phenyl]-1H-imidazol-4-yl}-methanone (118)

This compound is prepared by method C using compound 12i and 1-bromo-3-fluorobenzene {1-[3-(2-Fluoro-pyridin-3-yl)-phenyl]-1H-imidazol-4-yl}-(4-methoxy-phenyl)-methanone (119)

This compound is prepared by method C using compound 12i and 4-bromoanisole

{1-[3-(2-Fluoro-pyridin-3-yl)-phenyl]-1H-imidazol-4-yl}-(3-methoxy-phenyl)-methanone (120)

This compound is prepared by method C using compound 12i and 3-bromoanisole

{1-[3-(2-Fluoro-pyridin-3-yl)-phenyl]-1H-imidazol-4-yl}-(2-methoxy-phenyl)-methanone (121)

This compound is prepared by method C using compound 12i and 2-bromoanisole

{1-[3-(2-Fluoro-pyridin-3-yl)-phenyl]-1H-imidazol-4-yl}-thiazol-2-yl-methanone (122)

This compound is prepared by method C using compound 12i and thiazole

{1-[3-(2-Fluoro-pyridin-3-yl)-phenyl]-1H-imidazol-4-yl}-(5-methyl-thiazol-2-yl)-methanone (123)

This compound is prepared by method C using compound 12i and 5-methylthiazole

{1-[3-(2-Fluoro-pyridin-3-yl)-phenyl]-1H-imidazol-4-yl}-(1-methyl-1H-imidazol-2-yl)-methanone (124)

This compound is prepared by method C using compound 12i and 1-methylimidazole

{1-[3-(2-Fluoro-pyridin-3-yl)-phenyl]-1H-imidazol-4-yl}-furan-2-yl-methanone (125)

This compound is prepared by method C using compound 12i and furane

{1-[3-(2,4-Difluoro-pyridin-3-yl)-phenyl]-1H-imidazol-4-yl}-pyridin-2-yl-methanone (126)

This compound is prepared by method C using compound 12j and 2-bromopyridine

{1-[3-(2,4-Difluoro-pyridin-3-yl)-phenyl]-1H-imidazol-4-yl}-(3-methyl-pyridin-2-yl)-methanone (127)

This compound is prepared by method C using compound 12j and 2-bromo-3-methylpyridine {1-[3-(2,4-Difluoro-pyridin-3-yl)-phenyl]-1H-imidazol-4-yl}-(4-methyl-pyridin-2-yl)-methanone (128)

This compound is prepared by method C using compound 12j and 2-bromo-4-methylpyridine {1-[3-(2,4-Difluoro-pyridin-3-yl)-phenyl]-1H-imidazol-4-yl}-pyrimidin-2-yl-methanone (129)

This compound is prepared by method C using compound 12j and 2-bromopyrimidine (1-[3-(2,4-Difluoro-pyridin-3-yl)-phenyl]-1H-imidazol-4-yl)-(4-fluoro-phenyl)-methanone (130)

This compound is prepared by method C using compound 12j and 1-bromo-4-fluorobenzene {1-[3-(2,4-Difluoro-pyridin-3-yl)-phenyl]-1H-imidazol-4-yl}-(3-fluoro-phenyl)-methanone (131)

This compound is prepared by method C using compound 12j and 1-bromo-3-fluorobenzene {1-[3-(2,4-Difluoro-pyridin-3-yl)-phenyl]-1H-imidazol-4-yl}-(4-methoxy-phenyl)-methanone (132)

This compound is prepared by method C using compound 12j and 4-bromoanisole

{1-[3-(2,4-Difluoro-pyridin-3-yl)-phenyl]-1H-imidazol-4-yl}-(3-methoxy-phenyl)-methanone (133)

This compound is prepared by method C using compound 12j and 3-bromoanisole

{1-[3-(2,4-Difluoro-pyridin-3-yl)-phenyl]-1H-imidazol-4-yl}-(2-methoxy-phenyl)-methanone (134)

This compound is prepared by method C using compound 12j and 2-bromoanisole (1-[3-(2,4-Difluoro-pyridin-3-yl)-phenyl]-1H-imidazol-4-yl)-thiazol-2-yl-methanone (135)

This compound is prepared by method C using compound 12j and thiazole

{1-[3-(2,4-Difluoro-pyridin-3-yl)-phenyl]-1H-imidazol-4-yl}-(5-methyl-thiazol-2-yl)-methanone (136)

This compound is prepared by method C using compound 12j and 5-methylthiazole

{1-[3-(2,4-Difluoro-pyridin-3-yl)-phenyl]-1H-imidazol-4-yl}-(1-methyl-1H-imidazol-2-yl)-methanone (137)

This compound is prepared by method C using compound 12j and 1-methylimidazole

{1-[3-(2,4-Difluoro-pyridin-3-yl)-phenyl]-1H-imidazol-4-yl}-furan-2-yl-methanone (138)

This compound is prepared by method C using compound 12j and furane

{1-[3-(3-Fluoro-pyridin-4-yl)-phenyl]-1H-imidazol-4-yl}-pyridin-2-yl-methanone (139)

This compound is prepared by method C using compound 12k and 2-bromopyridine

{1-[3-(3-Fluoro-pyridin-4-yl)-phenyl]-1H-imidazol-4-yl}-(3-methyl-pyridin-2-yl)-methanone (140)

This compound is prepared by method C using compound 12k and 2-bromo-3-methylpyridine {1-[3-(3-Fluoro-pyridin-4-yl)-phenyl]-1H-imidazol- 4-yl}-(4-methyl-pyridin-2-yl)-methanone (141)

This compound is prepared by method C using compound 12k and 2-bromo-4-methylpyridine {1-[3-(3-Fluoro-pyridin-4-yl)-phenyl]-1H-imidazol-4-yl}-pyrimidin-2-yl-methanone (142)

This compound is prepared by method C using compound 12k and 2-bromopyrimidine

{4-Fluoro-phenyl)-1-[3-(3-fluoro-pyridin-4-yl)-phenyl]-1H-imidazol-4-yl}-methanone (143)

This compound is prepared by method C using compound 12k and 1-bromo-4-fluorobenzene (3-Fluoro-phenyl)-{1-[3-(3-fluoro-pyridin-4-yl)-phenyl]-1H-imidazol-4-yl}-methanone (144)

This compound is prepared by method C using compound 12k and 1-bromo-3-fluorobenzene {1-[3-(3-Fluoro-pyridin-4-yl)-phenyl]-1H-imidazol-4-yl}-(4-methoxy-phenyl)-methanone (145)

This compound is prepared by method C using compound 12k and 4-bromoanisole

{1-[3-(3-Fluoro-pyridin-4-yl)-phenyl]-1H-imidazol-4-yl}-(3-methoxy-phenyl)-methanone (146)

This compound is prepared by method C using compound 12k and 3-bromoanisole

{1-[3-(3-Fluoro-pyridin-4-yl)-phenyl]-1H-imidazol-4-yl}-(2-methoxy-phenyl)-methanone (147)

This compound is prepared by method C using compound 12k and 2-bromoanisole

{1-[3-(3-Fluoro-pyridin-4-yl)-phenyl]-1H-imidazol-4-yl}-thiazol-2-yl-methanone (148)

This compound is prepared by method C using compound 12k and thiazole

{1-[3-(3-Fluoro-pyridin-4-yl)-phenyl]-1H-imidazol-4-yl}-(5-methyl-thiazol-2-yl)-methanone (149)

This compound is prepared by method C using compound 12k and 5-methylthiazole

{1-[3-(3-Fluoro-pyridin-4-yl)-phenyl]-1H-imidazol-4-yl}-(1-methyl-1H-imidazol-2-yl)-methanone (150)

This compound is prepared by method C using compound 12k and 1-methylimidazole

{1-[3-(3-Fluoro-pyridin-4-yl)-phenyl]-1H-imidazol-4-yl}-furan-2-yl-methanone (151)

This compound is prepared by method C using compound 12k and furane

{1-[3-(2-Chloro-pyridin-3-yl)-phenyl]-1H-imidazol-4-yl}-pyridin-2-yl-methanone (152)

This compound is prepared by method C using compound 12l and 2-bromopyridine

{1-[3-(2-Chloro-pyridin-3-yl)-phenyl]-1H-imidazol-4-yl}-(3-methyl-pyridin-2-yl)-methanone (153)

This compound is prepared by method C using compound 12l and 2-bromo-3-methylpyridine {1-[3-(2-Chloro-pyridin-3-yl)-phenyl]-1H-imidazol-4-yl}-(4-methyl-pyridin-2-yl)-methanone (154)

This compound is prepared by method C using compound 12l and 2-bromo-4-methylpyridine {1-[3-(2-Chloro-pyridin-3-yl)-phenyl]-1H-imidazol-4-yl}-pyrimidin-2-yl-methanone (155)

This compound is prepared by method C using compound 12l and 2-bromopyrimidine (4-Fluoro-phenyl)-{1-[3-(2-chloro-pyridin-3-yl)-phenyl]-1H-imidazol-4-yl}-methanone (156)

This compound is prepared by method C using compound 12l and 1-bromo-4-fluorobenzene (3-Fluoro-phenyl){1-[3-(2-chloro-pyridin-3-yl)-phenyl]-1H-imidazol-4-yl}-methanone (157)

This compound is prepared by method C using compound 12l and 1-bromo-3-fluorobenzene {1-[3-(2-Chloro-pyridin-3-yl)-phenyl]-1H-imidazol-4-yl}-(4-methoxy-phenyl)-methanone (158)

This compound is prepared by method C using compound 12l and 4-bromoanisole

{1-[3-(2-Chloro-pyridin-3-yl)-phenyl]-1H-imidazol-4-yl}-(3-methoxy-phenyl)-methanone (159)

This compound is prepared by method C using compound 12l and 3-bromoanisole

{1-[3-(2-Chloro-pyridin-3-yl)-phenyl]-1H-imidazol-4-yl}-(2-methoxy-phenyl)-methanone (160)

This compound is prepared by method C using compound 12l and 2-bromoanisole

{1-[3-(2-Chloro-pyridin-3-yl)-phenyl]-1H-imidazol-4-yl}-thiazol-2-yl-methanone (161)

This compound is prepared by method C using compound 12l and thiazole

{1-[3-(2-Chloro-pyridin-3-yl)-phenyl]-1H-imidazol-4-yl}-(5-methyl-thiazol-2-yl)-methanone (162)

This compound is prepared by method C using compound 12l and 5-methylthiazole

{1-[3-(2-Chloro-pyridin-3-yl)-phenyl]-1H-imidazol-4-yl}-(1-methyl-1H-imidazol-2-yl)-methanone (163)

This compound is prepared by method C using compound 12l and 1-methylimidazole

{1-[3-(2-Chloro-pyridin-3-yl)-phenyl]-1H-imidazol-4-yl}-furan-2'-yl-methanone (164)

This compound is prepared by method C using compound 12l and furane

{1-[3-(2,4-Dimethoxy-pyrimidin-5-yl)-phenyl]-1H-imidazol-4-yl}-pyridin-2-yl-methanone (165)

This compound is prepared by method C using compound 12m and 2-bromopyridine

{1-[3-(2,4-Dimethoxy-pyrimidin-5-yl)-phenyl]-1H-imidazol-4-yl}-(3-methyl-pyridin-2-yl)-methanone (166)

This compound is prepared by method C using compound 12m and 2-bromo-3-methylpyridine (1-[3-(2,4-Dimethoxy-pyrimidin-5-yl)-phenyl]-1H-imidazol-4-yl)-(4-methyl-pyridin-2-yl)-methanone (167)

This compound is prepared by method C using compound 12m and 2-bromo-4-methylpyridine {1-[3-(2,4-Dimethoxy-pyrimidin-5-yl)-phenyl]-1H-imidazol-4-yl}-pyrimidin-2-yl-methanone (168)

This compound is prepared by method C using compound 12m and 2-bromopyrimidine

{1-[3-(2,4-Dimethoxy-pyrimidin-5-yl)-phenyl]-1H-imidazol-4-yl}-(4-fluoro-phenyl)-methanone (169)

This compound is prepared by method C using compound 12m and 1-bromo-4-fluorobenzene {1-[3-(2,4-Dimethoxy-pyrimidin-5-yl)-phenyl]-1H-imidazol-4-yl}-(3-fluoro-phenyl)-methanone (170)

This compound is prepared by method C using compound 12m and 1-bromo-3-fluorobenzene {1-[3-(2,4-Dimethoxy-pyrimidin-5-yl)-phenyl]-1H-imidazol-4-yl}-(4-methoxy-phenyl)-methanone (171)

This compound is prepared by method C using compound 12m and 4-bromoanisole

{1-[3-(2,4-Dimethoxy-pyrimidin-5-yl)-phenyl]-1H-imidazol-4-yl}-(3-methoxy-phenyl)-methanone (172)

This compound is prepared by method C using compound 12m and 3-bromoanisole

{1-[3-(2,4-Dimethoxy-pyrimidin-5-yl)-phenyl]-1H-imidazol-4-yl}-(2-methoxy-phenyl)-methanone (173)

This compound is prepared by method C using compound 12m and 2-bromoanisole

{1-[3-(2,4-Dimethoxy-pyrimidin-5-yl)-phenyl]-1H-imidazol-4-yl}-thiazol-2-yl-methanone (174)

This compound is prepared by method C using compound 12m and thiazole

{1-[3-(2,4-Dimethoxy-pyrimidin-5-yl)-phenyl]-1H-imidazol-4-yl}-(5-methyl-thiazol-2-yl)-methanone (175)

This compound is prepared by method C using compound 12m and 5-methylthiazole

{1-[3-(2,4-Dimethoxy-pyrimidin-5-yl)-phenyl]-1H-imidazol-4-yl})-(1-methyl-1H-imidazol-2-yl)-methanone (176)

This compound is prepared by method C using compound 12m and 1-methylimidazole

{1-[3-(2,4-Dimethoxy-pyrimidin-5-yl)-phenyl]-1H-imidazol-4-yl}-furan-2-yl-methanone (177)

This compound is prepared by method C using compound 12m and furane

Example 5

The Synthesis of Compounds 178-180 is Shown in Scheme 5

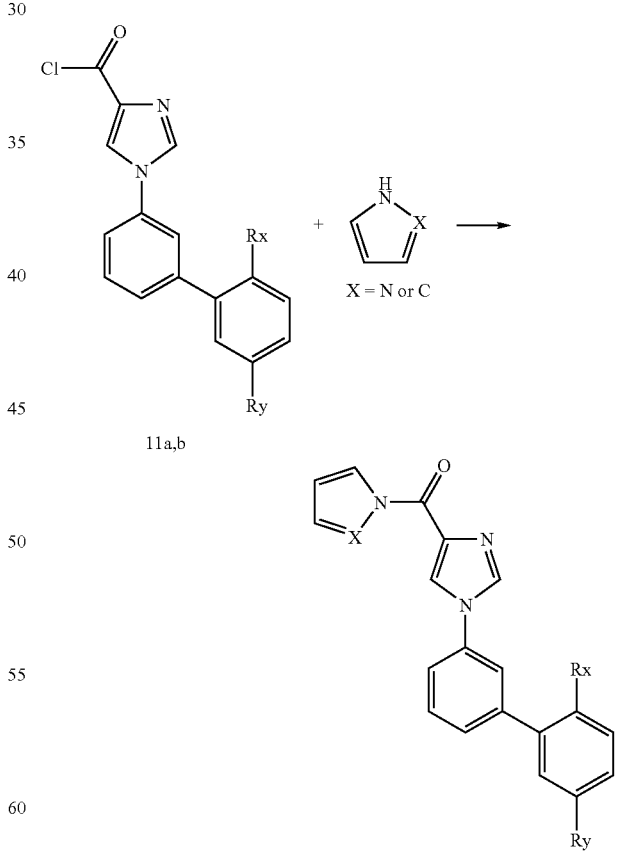

Amide Formation

Method D

(1-Biphenyl-3-yl-1H-imidazol-4-yl)-pyrazol-1-yl-methanone (178)

To a stirred, ice-cooled solution of sodium hydride (45 mg, 1.14 mmol) in anhydrous DMF (10 ml) was added pyrazole (77 mg, 1.14 mmol) and stirring was continued for 30 min. under nitrogen. A solution of compound 11a (0.27 g, 0.95 mmol) in DMF (10 ml) was added slowly and the resultant mixture was stirred at ambient conditions overnight. Water (80 ml) was added and the mixture was extracted with ethyl acetate. The extract was concentrated under reduced pressure and the concentrate was purified by column chromatography on silica gel eluting with a mixture of ethyl acetate and petroleum ether (1:1) to afford 178. (60 mg, 20%). Mp 124-127° C.

[1-(5'-Fluoro-2'-methoxy-biphenyl-3-yl)-1H-imidazol-4-yl]-pyrazol-1-yl-methanone (179)

This compound was prepared by method D using compound 11b.

[1-(5'-Fluoro-2'-methoxy-biphenyl-3-yl)-1H-imidazol-4-yl]-pyrrol-1-yl-methanone (180)

This compound was prepared by method D using compound 11b and pyrrole.

Test Methods

In Vitro Inhibition of 1H-flunitrazepam (3H-FNM) Binding

The GABA recognition site and the benzodiazepine modulatory unit can selectively be labelled with $^3$H-flunitrazepam.

Tissue Preparation

Preparations are performed at 0-4° C. unless otherwise indicated. Cerebral cortex from male Wistar rats (150-200 g) is homogenised for 5-10 sec in 20 ml Tris-HCl (30 mM, pH 7.4) using an Ultra-Turrax homogeniser. The suspension is centrifuged at 27,000×g for 15 min and the pellet is washed three times with buffer (centrifuged at 27,000×g for 10 min). The washed pellet is homogenized in 20 ml of buffer and incubated on a water bath (37° C.) for 30 min to remove endogenous GABA and then centrifuged for 10 min at 27,000×g. The pellet is then homogenized in buffer and centrifuged for 10 min at 27,000×g. The final pellet is resuspended in 30 ml buffer and the preparation is frozen and stored at −20° C.

Assay

The membrane preparation is thawed and centrifuged at 2° C. for 10 min at 27,000×g. The pellet is washed twice with 20 ml 50 mM Tris-citrate, pH 7.1 using an Ultra-Turrax homogeniser and centrifuged for 10 min at 27,000×g. The final pellet is resuspended in 50 mM Tris-citrate, pH 7.1 (500 ml buffer per g of original tissue), and then used for binding assays. Aliquots of 0.5 ml tissue are added to 25 µl of test solution and 25 µl of $^3$H-FNM (1 nM, final concentration), mixed and incubated for 40 min at 2° C. Non-specific binding is determined using Clonazepam (1 µM, final concentration). After incubation the samples are added 5 ml of ice-cold buffer and poured directly onto Whatman GF/C glass fibre filters under suction and immediately washed with 5 ml ice-cold buffer. The amount of radioactivity on the filters is determined by conventional liquid scintillation counting. Specific binding is total binding minus non-specific binding.

Results 25-75% inhibition of specific binding must be obtained, before calculation of an $IC_{50}$.

The test value will be given as $IC_{50}$ (the concentration (µM) of the test substance which inhibits the specific binding of $^3$H-FNM by 50%).

$$IC_{50} = (\text{applied test substance concentration, }\mu M) \times \frac{1}{\left(\frac{C_0}{C_x} - 1\right)}$$

where
$C_o$ is specific binding in control assays, and
$C_x$ is the specific binding in the test assay.
(The calculations assume normal mass-action kinetics).

Test results from these experiments with a number of compounds of the invention are shown in Table 1 below.

TABLE 1

| Test compound | In vitro binding $IC_{50}$ (µM) |
|---|---|
| Compound 8 | 0.036 |
| Compound 14 | 0.0027 |
| Compound 178 | 0.0059 |

The invention claimed is:

1. A compound of the general formula (I):

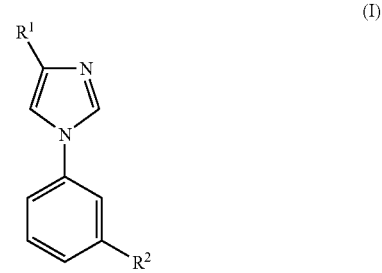

any of its stereoisomers or any mixture of its stereoisomers, or a pharmaceutically acceptable salt thereof, wherein $R^1$ represents —$COR^3$; wherein $R^3$ represents —$(CH_2$—$O)_m$-aryl or —$(CH_2$—$O)_m$-heteroaryl; wherein m is 0 or 1; and which aryl or heteroaryl group is optionally substituted with one or more substituents independently selected from the group consisting of: halo, hydroxy, $R^aR^bN$—, $R^aR^bN$-alkyl, cyano, nitro, trifluoromethyl, trifluoromethoxy, alkoxy, cycloalkoxy, $R^a$—(C=O)—, $R^a$—O—(C=O)—, alkyl, cycloalkyl, cycloalkylalkyl, alkenyl, and alkynyl; wherein $R^a$ and $R^b$ independent of each other are hydrogen or alkyl; and $R^2$ represents halo, nitro, aryl or heteroaryl; which aryl or heteroaryl group is optionally substituted with one or more substituents independently selected from the group consisting of: halo, hydroxy, $R^dR^eN$—, $R^dR^eN$-alkyl, $R^dR^eN$—(C=O)—, cyano, nitro, trifluoromethyl, trifluoromethoxy, alkoxy, cycloalkoxy, $R^d$—(C=O)—, $R^d$—O—(C=O)—, alkyl, cycloalkyl, cycloalkylalkyl, alkenyl, and alkynyl; wherein $R^d$ and $R^e$ independent of each other are hydrogen or alkyl.

2. The compound of claim 1, or a pharmaceutically acceptable salt thereof, wherein $R^1$ represents —$COR^3$; wherein $R^3$ represents —$(CH_2$—$O)_m$-aryl which aryl group is optionally substituted with one or more substituents independently selected from the group consisting of: halo, hydroxy, $R^aR^bN$—, $R^aR^bN$-alkyl, cyano, nitro, trifluoromethyl, trifluoromethoxy, alkoxy, cycloalkoxy, $R^a$—(C=O)—, $R^a$—O—(C=O)—, alkyl, cycloalkyl, cycloalkylalkyl, alkenyl, and alkynyl; wherein $R^a$ and $R^b$ independent of each other are hydrogen or alkyl.

3. The compound of claim 1, or a pharmaceutically acceptable salt thereof, wherein $R^1$ represents —$COR^3$; wherein $R^3$ represents —$(CH_2-O)_m$-heteroaryl which heteroaryl group is optionally substituted with one or more substituents independently selected from the group consisting of: halo, hydroxy, $R^aR^bN$—, $R^aR^bN$-alkyl, cyano, nitro, trifluoromethyl, trifluoromethoxy, alkoxy, cycloalkoxy, $R^a$—O—(C=O)—, alkyl, cycloalkyl, cycloalkylalkyl, alkenyl, and alkynyl; wherein $R^a$ and $R^b$ independent of each other are hydrogen or alkyl.

4. The compound of claim 1, or a pharmaceutically acceptable salt thereof, wherein $R^2$ represents halo or nitro.

5. The compound of claim 1, or a pharmaceutically acceptable salt thereof, wherein $R^2$ represents aryl, which aryl group is optionally substituted with one or more substituents independently selected from the group consisting of: halo, hydroxy, $R^dR^eN$—, $R^dR^eN$-alkyl, $R^dR^eN$—(C=O)—, cyano, nitro, trifluoromethyl, trifluoromethoxy, alkoxy, cycloalkoxy, $R^d$—(C=O)—, $R^d$—O—(C=O)—, alkyl, cycloalkyl, cycloalkylalkyl, alkenyl, and alkynyl; wherein $R^d$ and $R^e$ independent of each other are hydrogen or alkyl.

6. The compound of claim 1, which is selected from
1-[1-(3-Bromo-phenyl)-1H-imidazol-4-yl]-2-(pyridin-3-yloxy)-ethanone;
[1-(3-Bromo-phenyl)-1H-imidazol-4-yl]-phenyl-methanone;
(1-Biphenyl-3-yl-1H-imidazol-4-yl)-phenyl-methanone;
(1-Biphenyl-3-yl-1H-imidazol-4-yl)-pyridin-2-yl-methanone;
[1-(5'-Fluoro-2'-methoxy-biphenyl-3-yl)-1H-imidazol-4-yl]-pyridin-2-yl-methanone;
[1-(5'-Fluoro-2'-methoxy-biphenyl-3-yl)-1H-imidazol-4-yl]-(3-methyl-pyridin-2-yl)-methanone;
[1-(5'-Fluoro-2'-methoxy-biphenyl-3-yl)-1H-imidazol-4-yl]-(4-methyl-pyridin-2-yl)-methanone;
[1-(5'-Fluoro-2'-methoxy-biphenyl-3-yl)-1H-imidazol-4-yl]-pyrimidin-2-yl-methanone;
(1-Biphenyl-3-yl-1H-imidazol-4-yl)-(4-fluoro-phenyl)-methanone;
(1-Biphenyl-3-yl-1H-imidazol-4-yl)-(3-fluoro-phenyl)-methanone;
(1-Biphenyl-3-yl-1H-imidazol-4-yl)-(4-methoxy-phenyl)-methanone;
(1-Biphenyl-3-yl-1H-imidazol-4-yl)-(3-methoxy-phenyl)-methanone;
(1-Biphenyl-3-yl-1H-imidazol-4-yl)-(2-methoxy-phenyl)-methanone;
(1-Biphenyl-3-yl-1H-imidazol-4-yl)-thiazol-2-yl-methanone;
(1-Biphenyl-3-yl-1H-imidazol-4-yl)-furan-2-yl-methanone;
[1-(5'-Fluoro-2'-methoxy-biphenyl-3-yl)-1H-imidazol-4-yl]-thiazol-2-yl-methanone;
[1-(5'-Fluoro-2'-methoxy-biphenyl-3-yl)-1H-imidazol-4-yl]-furan-2-yl-methanone;
[1-(5'-Fluoro-2'-methoxy-biphenyl-3-yl)-1H-imidazol-4-yl]-(5-methyl-thiazol-2-yl)-methanone;
[1-(5'-Fluoro-2'-methoxy-biphenyl-3-yl)-1H-imidazol-4-yl]-(1-methyl-imidazol-2-yl)-methanone;
(1-Ethoxymethyl-1H-imidazol-2-yl)-[1-(5'-fluoro-2'-methoxy-biphenyl-3-yl)-1H-imidazol-4-yl]-methanone;
(1-Ethyl-1H-imidazol-2-yl)-[1-(5'-fluoro-2'-methoxy-biphenyl-3-yl)-1H-imidazol-4-yl]methanone;
(1-i-Propyl-1H-imidazol-2-yl)-[1-(5'-fluoro-2'-methoxy-biphenyl-3-yl)-1H-imidazol-4-yl]-methanone;
(1-(2-Hydroxyethyl)-1H-imidazol-2-yl)-[1-(5'-fluoro-2'-methoxy-biphenyl-3-yl)-1H-imidazol-4-yl]-methanone;
(1-(2-Methoxyethyl)-1H-imidazol-2-yl)-[1-(5'-fluoro-2'-methoxy-biphenyl-3-yl)-1H-imidazol-4-yl]-methanone;
[1-(2'-Methoxy-biphenyl-3-yl)-1H-imidazol-4-yl]-pyridin-2-yl-methanone;
[1-(2'-Methoxy-biphenyl-3-yl)-1H-imidazol-4-yl]-(3-methyl-pyridin-2-yl)-methanone;
[1-(2'-Methoxy-biphenyl-3-yl)-1H-imidazol-4-yl]-(4-methyl-pyridin-2-yl)-methanone;
[1-(2'-Methoxy-biphenyl-3-yl)-1H-imidazol-4-yl]-pyrimidin-2-yl-methanone;
(4-Fluoro-phenyl)-[1-(2'-methoxy-biphenyl-3-yl)-1H-imidazol-4-yl]-methanone;
(3-Fluoro-phenyl)-[1-(2'-methoxy-biphenyl-3-yl)-1H-imidazol-4-yl]-methanone;
(4-Methoxy-phenyl)-[1-(2'-methoxy-biphenyl-3-yl)-1H-imidazol-4-yl]-methanone;
(3-Methoxy-phenyl)-[1-(2'-methoxy-biphenyl-3-yl)-1H-imidazol-4-yl]-methanone;
(2-Methoxy-phenyl)-[1-(2'-methoxy-biphenyl-3-yl)-1H-imidazol-4-yl]methanone;
[1-(2'-Methoxy-biphenyl-3-yl)-1H-imidazol-4-yl]-thiazol-2-yl-methanone;
[1-(2'-Methoxy-biphenyl-3-yl)-1H-imidazol-4-yl]-(5-methyl-thiazol-2-yl)-methanone;
[1-(2'-Methoxy-biphenyl-3-yl)-1H-imidazol-4-yl]-(1-methyl-imidazol-2-yl)-methanone;
Furan-2-yl-[1-(2'-methoxy-biphenyl-3-yl)-1H-imidazol-4-yl]-methanone;
3'-[4-(Pyridine-2-carbonyl)-imidazol-1-yl]-biphenyl-2-carbonitrile;
3'-[4-(3-Methyl-pyridine-2-carbonyl)-imidazol-1-yl]-biphenyl-2-carbonitrile;
3'-[4-(4-Methyl-pyridine-2-carbonyl)-imidazol-1-yl]-biphenyl-2-carbonitrile;
3'-[4-(Pyrimidine-2-carbonyl)-imidazol-1-yl]-biphenyl-2-carbonitrile;
3-[4-(4-Fluoro-benzoyl)-imidazol-1-yl]-biphenyl-2-carbonitrile;
3'-[4-(3-Fluoro-benzoyl)-imidazol-1-yl]-biphenyl-2-carbonitrile;
3'-[4-(4-Methoxy-benzoyl)-imidazol-1-yl]-biphenyl-2-carbonitrile;
3'-[4-(3-Methoxy-benzoyl)-imidazol-1-yl]-biphenyl-2-carbonitrile;
3'-[4-(2-Methoxy-benzoyl)-imidazol-1-yl]-biphenyl-2-carbonitrile;
3'-[4-(Thiazole-2-carbonyl)-imidazol-1-yl]-biphenyl-2-carbonitrile;
3'-[4-(5-Methyl-thiazole-2-carbonyl)-imidazol-1-yl]-biphenyl-2-carbonitrile;
3'-[4-(1-Methyl-1H-imidazole-2-carbonyl)-imidazol-1-yl]-biphenyl-2-carbonitrile;
3'-[4-(Furan-2-carbonyl)-imidazol-1-yl]-biphenyl-2-carbonitrile;
[1-(2'-Chloro-biphenyl-3-yl)-1H-imidazol-4-yl]-pyridin-2-yl-methanone;
[1-(2'-Chloro-biphenyl-3-yl)-1H-imidazol-4-yl]-(3-methyl-pyridin-2-yl)-methanone;
[1-(2'-Chloro-biphenyl-3-yl)-1H-imidazol-4-yl]-(4-methyl-pyridin-2-yl)-methanone;
[1-(2'-Chloro-biphenyl-3-yl)-1H-imidazol-4-yl]-pyrimidin-2-yl-methanone;
[1-(2'-Chloro-biphenyl-3-yl)-1H-imidazol-4-yl]-(4-fluoro-phenyl)-methanone;
[1-(2'-Chloro-biphenyl-3-yl)-1H-imidazol-4-yl]-(3-fluoro-phenyl)-methanone;
[1-(2'-Chloro-biphenyl-3-yl)-1H-imidazol-4-yl]-(4-methoxy-phenyl)-methanone;
[1-(2'-Chloro-biphenyl-3-yl)-1H-imidazol-4-yl]-(3-methoxy-phenyl)-methanone;
[1-(2'-Chloro-biphenyl-3-yl)-1H-imidazol-4-yl]-(2-methoxy-phenyl)-methanone;
[1-(2'-Chloro-biphenyl-3-yl)-1H-imidazol-4-yl]-thiazol-2-yl-methanone;
[1-(2'-Chloro-biphenyl-3-yl)-1H-imidazol-4-yl]-(5-methyl-thiazol-2-yl)-methanone;
[1-(2'-Chloro-biphenyl-3-yl)-1H-imidazol-4-yl]-(1-methyl-1H-imidazol-2-yl)-methanone;
[1-(2'-Chloro-biphenyl-3-yl)-1H imidazol-4-yl]-furan-2-yl-methanone;
Pyridin-2-yl-[1-(2'-trifluoromethoxy-biphenyl-3-yl)-1H-imidazol-4-yl]-methanone;
(3-Methyl-pyridin-2-yl)-[1-(2'-trifluoromethoxy-biphenyl-3-yl)-1H-imidazol-4-yl]-methanone;
(4-Methyl-pyridin-2-yl)-[1-(2'-trifluoromethoxy-biphenyl-3-yl)-1H-imidazol-4-yl]-methanone;
Pyrimidin-2-yl-[1-(2'-trifluoromethoxy-biphenyl-3-yl)-1H-imidazol-4-yl]-methanone;
(4-Fluoro-phenyl)-[1-(2'-trifluoromethoxy-biphenyl-3-yl)-1H-imidazol-4-yl]-methanone;
(3-Fluoro-phenyl)-[1-(2'-trifluoromethoxy-biphenyl-3-yl)-1H-imidazol-4-yl]-methanone;
(4-Methoxy-phenyl)-[1-(2'-trifluoromethoxy-biphenyl-3-yl)-1H-imidazol-4-yl]-methanone;
(3-Methoxy-phenyl)-[1-(2'-trifluoromethoxy-biphenyl-3-yl)-1H-imidazol-4-yl]-methanone;
(2-Methoxy-phenyl)-[1-(2'-trifluoromethoxy-biphenyl-3-yl)-1H-imidazol-4-yl]-methanone;
Thiazol-2-yl-[1-(2'-trifluoromethoxy-biphenyl-3-yl)-1H-imidazol-4-yl]-methanone;
(5-Methyl-thiazol-2-yl)-[1-(2'-trifluoromethoxy-biphenyl-3-yl)-1H-imidazol-4-yl]-methanone;
(1-Methyl-1H-Imidazol-2-yl)-[1-(2'-trifluoromethoxy-biphenyl-3-yl)-1H-imidazol-4-yl]-methanone;
Furan-2-yl-[1-(2'-trifluoromethoxy-biphenyl-3-yl)-1H-imidazol-4-yl]-methanone;
[1-(6'-Fluoro-2'-methoxy-biphenyl-3-yl)-1H-imidazol-4-yl]-pyridin-2-yl-methanone;
[1-(6'-Fluoro-2'-methoxy-biphenyl-3-yl)-1H-imidazol-4-yl]-(3-methyl-pyridin-2-yl)-methanone;
[1-(6'-Fluoro-2'-methoxy-biphenyl-3-yl)-1H-imidazol-4-yl]-(4-methyl-pyridin-2-yl)-methanone;
[1-(6'-Fluoro-2'-methoxy-biphenyl-3-yl)-1H-imidazol-4-yl]-pyrimidin-2-yl-methanone;
[1-(6'-Fluoro-2'-methoxy-biphenyl-3-yl)-1H-imidazol-4-yl]-(4-fluoro-phenyl)-methanone;
[1-(6'-Fluoro-2'-methoxy-biphenyl-3-yl)-1H-imidazol-4-yl]-(3-fluoro-phenyl)-methanone;
[1-(6'-Fluoro-2'-methoxy-biphenyl-3-yl)-1H-imidazol-4-yl]-(4-methoxy-phenyl)-methanone;
[1-(6'-Fluoro-2'-methoxy-biphenyl-3-yl)-1H-imidazol-4-yl]-(3-methoxy-phenyl)-methanone;
[1-(6'-Fluoro-2'-methoxy-biphenyl-3-yl)-1H-imidazol-4-yl]-(2-methoxy-phenyl)-methanone;
[1-(6'-Fluoro-2'-methoxy-biphenyl-3-yl)-1H-imidazol-4-yl]-thiazol-2-yl-methanone;
[1-(6'-Fluoro-2'-methoxy-biphenyl-3-yl)-1H-imidazol-4-yl]-(5-methyl-thiazol-2-yl)-methanone;
[1-(6'-Fluoro-2'-methoxy-biphenyl-3-yl)-1H-imidazol-4-yl]-(1-methyl-1H-imidazol-2-yl)-methanone;
[1-(6'-Fluoro-2'-methoxy-biphenyl-3-yl)-1H-imidazol-4-yl]-furan-2-yl-methanone;
[1-(3'-Fluoro-2'-methoxy-biphenyl-3-yl)-1H-imidazol-4-yl]-pyridin-2-yl-methanone;
[1-(3'-Fluoro-2'-methoxy-biphenyl-3-yl)-1H-imidazol-4-yl]-(3-methyl-pyridin-2-yl)-methanone;
[1-(3'-Fluoro-2'-methoxy-biphenyl-3-yl)-1H-imidazol-4-yl]-(4-methyl-pyridin-2-yl)-methanone;
[1-(3'-Fluoro-2'-methoxy-biphenyl-3-yl)-1H-imidazol-4-yl]-pyrimidin-2-yl-methanone;
[1-(3'-Fluoro-2'-methoxy-biphenyl-3-yl)-1H-imidazol-4-yl]-(4-fluoro-phenyl)-methanone;
[1-(3'-Fluoro-2'-methoxy-biphenyl-3-yl)-1H-imidazol-4-yl]-(3-fluoro-phenyl)-methanone;
[1-(3'-Fluoro-2'-methoxy-biphenyl-3-yl)-1H-imidazol-4-yl]-(4-methoxy-phenyl)-methanone;
[1-(3'-Fluoro-2'-methoxy-biphenyl-3-yl)-1H-imidazol-4-yl]-(3-methoxy-phenyl)-methanone;
[1-(3'-Fluoro-2'-methoxy-biphenyl-3-yl)-1H-imidazol-4-yl]-(2-methoxy-phenyl)-methanone;
[1-(3'-Fluoro-2'-methoxy-biphenyl-3-yl)-1H-imidazol-4-yl]-thiazol-2-yl-methanone;
[1-(3'-Fluoro-2'-methoxy-biphenyl-3-yl)-1H-imidazol-4-yl]-(5-methyl-thiazol-2-yl)-methanone;
[1-(3'-Fluoro-2'-methoxy-biphenyl-3-yl)-1H-imidazol-4-yl]-(1-methyl-1H-imidazol-2-yl)-methanone;
[1-(3'-Fluoro-2'-methoxy-biphenyl-3-yl)-1H-imidazol-4-yl]-furan-2-yl-methanone;
{1-[3-(2-Fluoro-pyridin-3-yl)-phenyl]-1H-imidazol-4-yl}-pyridin-2-yl-methanone;
{1-[3-(2-Fluoro-pyridin-3-yl)-phenyl]-1H-imidazol-4-yl}-(3-methyl-pyridin-2-yl)-methanone;
{1-[3-(2-Fluoro-pyridin-3-yl)-phenyl]-1H-imidazol-4-yl}-(4-methyl-pyridin-2-yl)-methanone;
{1-[3-(2-Fluoro-pyridin-3-yl)-phenyl]-1H-imidazol-4-yl}-pyrimidin-2-yl-methanone;
(4-Fluoro-phenyl)-{1-[3-(2-fluoro-pyridin-3-yl)-phenyl]-1H-imidazol-4-yl}-methanone;
(3-Fluoro-phenyl)-{1-[3-(2-fluoro-pyridin-3-yl)-phenyl]-1H-imidazol-4-yl}-methanone;
{1-[3-(2-Fluoro-pyridin-3-yl)-phenyl]-1H-imidazol-4-yl}-(4-methoxy-phenyl)-methanone;
{1-[3-(2-Fluoro-pyridin-3-yl)-phenyl]-1H-imidazol-4-yl}-(3-methoxy-phenyl)-methanone;
{1-[3-(2-Fluoro-pyridin-3-yl)-phenyl]-1H-imidazol-4-yl}-(2-methoxy-phenyl)-methanone;
{1-[3-(2-Fluoro-pyridin-3-yl)-phenyl]-1H-imidazol-4-yl}-thiazol-2-yl-methanone;
{1-[3-(2-Fluoro-pyridin-3-yl)-phenyl]-1H-imidazol-4-yl}-(5-methyl-thiazol-2-yl)-methanone;
{1-[3-(2-Fluoro-pyridin-3-yl)-phenyl]-1H-imidazol-4-yl}-(1-methyl-1H-imidazol-2-yl)-methanone;
{1-[3-(2-Fluoro-pyridin-3-yl)-phenyl]-1H-imidazol-4-yl}-furan-2-yl-methanone;
{1-[3-(2,4-Difluoro-pyridin-3-yl)-phenyl]-1H-imidazol-4-yl}-pyridin-2-yl-methanone;
{1-[3-(2,4-Difluoro-pyridin-3-yl)-phenyl]-1H-imidazol-4-yl}-(3-methyl-pyridin-2-yl)-methanone;
{1-[3-(2,4-Difluoro-pyridin-3-yl)-phenyl]-1H-imidazol-4-yl}-(4-methyl-pyridin-2-yl)-methanone;
{1-[3-(2,4-Difluoro-pyridin-3-yl)-phenyl]-1H-imidazol- 4-yl}-pyrimidin-2-yl-methanone;
{1-[3-(2,4-Difluoro-pyridin-3-yl)-phenyl]-1H-imidazol-4-yl}-(4-fluoro-phenyl)-methanone;
{1-[3-(2,4-Difluoro-pyridin-3-yl)-phenyl]-1H-imidazol-4-yl}-(3-fluoro-phenyl)-methanone;
{1-[3-(2,4-Difluoro-pyridin-3-yl)-phenyl]-1H-imidazol-4-yl}-(4-methoxy-phenyl)-methanone;
{1-[3-(2,4-Difluoro-pyridin-3-yl)-phenyl]-1H-imidazol-4-yl}-(3-methoxy-phenyl)-methanone;
{1-[3-(2,4-Difluoro-pyridin-3-yl)-phenyl]-1H-imidazol-4-yl}-(2-methoxy-phenyl)-methanone;
{1-[3-(2,4-Difluoro-pyridin-3-yl)-phenyl]-1H-imidazol-4-yl}-thiazol-2-yl-methanone;
{1-[3-(2,4-Difluoro-pyridin-3-yl)-phenyl]-1H-imidazol-4-yl}-(5-methyl-thiazol-2-yl)-methanone;
{1-[3-(2,4-Difluoro-pyridin-3-yl)-phenyl]-1H-imidazol-4-yl}-(1-methyl-1H-imidazol-2-yl)-methanone;
{1-[3-(2,4-Difluoro-pyridin-3-yl)-phenyl]-1H-imidazol-4-yl}-furan-2-yl-methanone;
{1-[3-(3-Fluoro-pyridin-4-yl)-phenyl]-1H-imidazol-4-yl}-pyridin-2-yl-methanone;
{1-[3-(3-Fluoro-pyridin-4-yl)-phenyl]-1H-imidazol-4-yl}-(3-methyl-pyridin-2-yl)-methanone;
{1-[3-(3-Fluoro-pyridin-4-yl)-phenyl]-1H-imidazol-4-yl}-(4-methyl-pyridin-2-yl)-methanone;
{1-[3-(3-Fluoro-pyridin-4-yl)-phenyl]-1H-imidazol-4-yl}-pyrimidin-2-yl-methanone;
(4-Fluoro-phenyl)-{1-[3-(3-fluoro-pyridin-4-ye-phenyl]-1H-imidazol-4-yl}-methanone;
(3-Fluoro-phenyl)-{1-[3-(3-fluoro-pyridin-4-yl)-phenyl]-1H-imidazol-4-yl}-methanone;
{1-[3-(3-Fluoro-pyridin-4-yl)-phenyl]-1H-imidazol-4-yl}-(4-methoxy-phenyl)-methanone;
{1-[3-(3-Fluoro-pyridin-4-yl)-phenyl]-1H-imidazol-4-yl}-(3-methoxy-phenyl)-methanone;
{1-[3-(3-Fluoro-pyridin-4-yl)-phenyl]-1H-imidazol-4-yl}-(2-methoxy-phenyl)-methanone;
{1-[3-(3-Fluoro-pyridin-4-yl)-phenyl]-1H-imidazol-4-yl}-thiazol-2-yl-methanone;
{1-[3-(3-Fluoro-pyridin-4-yl)-phenyl]-1H-imidazol-4-yl}-(5-methyl-thiazol-2-yl)-methanone;
{1-[3-(3-Fluoro-pyridin-4-yl)-phenyl]-1H-imidazol-4-yl}-(1-methyl-1H-imidazol-2-yl)-methanone;
{1-[3-(3-Fluoro-pyridin-4-yl)-phenyl]-1H-imidazol-4-yl}-furan-2-yl-methanone;
{1-[3-(2-Chloro-pyridin-3-yl)-phenyl]-1H-imidazol-4-yl}-pyridin-2-yl-methanone;
{1-[3-(2-Chloro-pyridin-3-yl)-phenyl]-1H-imidazol-4-yl}-(3-methyl-pyridin-2-yl)-methanone;
{1-[3-(2-Chloro-pyridin-3-yl)-phenyl]-1H-imidazol-4-yl}-(4-methyl-pyridin-2-yl)-methanone;
{1-[3-(2-Chloro-pyridin-3-yl)-phenyl]-1H-imidazol-4-yl}-pyrimidin-2-yl-methanone;
(4-Fluoro-phenyl)-{1-[3-(2-chloro-pyridin-3-yl)-phenyl]-1H-imidazol-4-yl}-methanone;
(3-Fluoro-phenyl)-{1-[3-(2-chloro-pyridin-3-yl)phenyl]-1H-imidazol-4-yl}-methanone;
{1-[3-(2-Chloro-pyridin-3-yl)-phenyl]-1H-imidazol-4-yl}-(4-methoxy-phenyl)-methanone;
{1-[3-(2-Chloro-pyridin-3-yl)-phenyl]-1H-imidazol-4-yl}-(3-methoxy-phenyl)-methanone;
{1-[3-(2-Chloro-pyridin-3-yl)-phenyl]-1H-imidazol-4-yl}-(2-methoxy-phenyl)-methanone;
{1-[3-(2-Chloro-pyridin-3-yl)-phenyl]-1H-imidazol-4-yl}-thiazol-2-yl-methanone;
{1-[3-(2-Chloro-pyridin-3-yl)-phenyl]-1H-imidazol-4-yl}-(5-methyl-thiazol-2-yl)-methanone;
{1-[3-(2-Chloro-pyridin-3-yl)-phenyl]-1H-imidazol-4-yl}-(1-methyl-1H-imidazol-2-yl)-methanone;
{1-[3-(2-Chloro-pyridin-3-yl)-phenyl]-1H-imidazol-4-yl}-furan-2-yl-methanone;
{1-[3-(2,4-Dimethoxy-pyrimidin-5-yl)-phenyl]-1H-imidazol-4-yl}-pyridin-2-yl-methanone;
{1-[3-(2,4-Dimethoxy-pyrimidin-5-yl)-phenyl]-1H-imidazol-4-yl}-(3-methyl-pyridin-2-yl)-methanone;
{1-[3-(2,4-Dimethoxy-pyrimidin-5-yl)-phenyl]-1H-imidazol-4-yl}-(4-methyl-pyridin-2-yl)-methanone;
{1-[3-(2,4-Dimethoxy-pyrimidin-5-yl)-phenyl]-1H-imidazol-4-yl}-pyrimidin-2-yl-methanone;
{1-[3-(2,4-Dimethoxy-pyrimidin-5-yl)-phenyl]-1H-imidazol-4-yl}-(4-fluoro-phenyl)-methanone;
{1-[3-(2,4-Dimethoxy-pyrimidin-5-yl)-phenyl]-1H-imidazol-4-yl}-(3-fluoro-phenyl)-methanone;
{1-[3-(2,4-Dimethoxy-pyrimidin-5-yl)-phenyl]-1H-imidazol-4-yl}-(4-methoxy-phenyl)-methanone;
{1-[3-(2,4-Dimethoxy-pyrimidin-5-yl)-phenyl]-1H-imidazol-4-yl}-(3-methoxy-phenyl)-methanone;
{1-[3-(2,4-Dimethoxy-pyrimidin-5-yl)-phenyl]-1H-imidazol-4-yl}-(2-methoxy-phenyl)-methanone;
{1-[3-(2,4-Dimethoxy-pyrimidin-5-yl)-phenyl]-1H-imidazol-4-yl}-thiazol-2-yl-methanone;
{1-[3-(2,4-Dimethoxy-pyrimidin-5-yl)-phenyl]-1H-imidazol-4-yl}-(5-methyl-thiazol-2-yl)-methanone;
{1-[3-(2,4-Dimethoxy-pyrimidin-5-yl)-phenyl]-1H-imidazol-4-yl}-(1-methyl-1H-imidazol-2-yl)-methanone;
{1-[3-(2,4-Dimethoxy-pyrimidin-5-yl)-phenyl]-1H-imidazol-4-yl}-furan-2-yl-methanone;
(1-Biphenyl-3-yl-1H-imidazol-4-yl)-pyrazol-1-yl-methanone (178);
[1-(5'-Fluoro-2'-methoxy-biphenyl-3-yl)-1H-imidazol-4-yl]-pyrazol-1-yl-methanone; and
[1-(5'-Fluoro-2'-methoxy-biphenyl-3-yl)-1H-imidazol-4-yl]-pyrrol-1-yl-methanone; or
any of its stereoisomers or any mixture of its stereoisomers, or a pharmaceutically acceptable salt thereof.

7. A pharmaceutical composition, comprising a therapeutically effective amount of a compound of claim 1, any of its stereoisomers or any mixture of its stereoisomers, or a pharmaceutically acceptable salt thereof, together with at least one pharmaceutically acceptable carrier, excipient or diluent.

8. The compound of claim 6, which is [1-(5'-fluoro-2'-methoxybiphenyl-3-yl)-1H-imidazol-4-yl]-(1-methylimidazol-2-yl)-methanone, or any of its stereoisomers or any mixture of its stereoisomers, or a pharmaceutically acceptable salt thereof.

* * * * *